(12) United States Patent
Huang et al.

(10) Patent No.: US 6,890,557 B2
(45) Date of Patent: May 10, 2005

(54) EMULSION FORMULATIONS FOR HYDROPHILIC ACTIVE AGENTS

(75) Inventors: Leaf Huang, Wexford, PA (US); Toshifumi Hara, Chofu (JP)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 10/444,651

(22) Filed: May 22, 2003

(65) Prior Publication Data

US 2003/0224041 A1 Dec. 4, 2003

Related U.S. Application Data

(63) Continuation of application No. 09/214,546, filed as application No. PCT/US97/12544 on Jul. 3, 1997, now Pat. No. 6,610,321, which is a continuation of application No. 08/676,867, filed on Jul. 3, 1996, now abandoned.

(51) Int. Cl.$^7$ .............................................. A61K 9/127
(52) U.S. Cl. ........................ 424/450; 424/400; 514/44
(58) Field of Search ................................ 424/450, 400; 514/44, 937–943; 428/402.2; 264/4.1, 4.3, 4.6

(56) References Cited

U.S. PATENT DOCUMENTS

| | | | |
|---|---|---|---|
| 4,868,158 A | * 9/1989 | Masquelier et al. | 514/21 |
| 5,283,185 A | 2/1994 | Epand et al. | |
| 5,324,821 A | * 6/1994 | Favre et al. | 530/359 |
| 5,374,548 A | 12/1994 | Caras | |
| 5,523,222 A | 6/1996 | Page et al. | |
| 5,540,933 A | 7/1996 | Ruoslahti et al. | |
| 5,545,412 A | 8/1996 | Eppstein et al. | |
| 5,576,016 A | * 11/1996 | Amselem et al. | 424/450 |
| 5,578,475 A | * 11/1996 | Jessee | 435/456 |
| 5,578,583 A | * 11/1996 | Maranh ao | 514/49 |
| 5,635,487 A | 6/1997 | Wolff et al. | |
| 5,676,954 A | 10/1997 | Brigham | |
| 5,756,353 A | 5/1998 | Debs | |
| 5,795,587 A | 8/1998 | Gao et al. | |
| 5,827,703 A | 10/1998 | Debs et al. | |
| 5,877,302 A | 3/1999 | Hanson et al. | |
| 6,008,336 A | 12/1999 | Hanson et al. | |
| 6,077,835 A | 6/2000 | Hanson et al. | |

FOREIGN PATENT DOCUMENTS

| | | |
|---|---|---|
| EP | 0 387 647 | 9/1990 |
| FR | 2 649 321 | 1/1991 |
| WO | WO 90/03164 | * 4/1990 |
| WO | WO 93/05162 | 3/1993 |
| WO | WO 93/18852 | 9/1993 |
| WO | WO94/26252 | * 11/1994 |
| WO | WO 94/26252 | 11/1994 |
| WO | WO 95/25809 | 9/1995 |
| WO | WO 95/31181 | * 11/1995 |
| WO | WO 97/11682 | 4/1997 |
| WO | WO 97/39019 | 10/1997 |
| WO | WO 98/00110 | 1/1998 |

OTHER PUBLICATIONS

Sautereau et al. European Journal of Pharmaceutics and Biopharmaceutics. vol. 41, Apr. 1995, No. 2, pp. 136–139.*
Bijsterbosch, M. K. et al., (1990), "Native and Modified Lipoproteins as Drug Delivery Systems," *Adv. Drug Delivery Revs.* 5:231–251.
Bijsterborch, M. K. et al., (1992). "Lactosylated High Density Lipoprotein: A Potential Carrier For the Site–Specific Delivery of Drugs to Parenchymal Liver Cells," *Mol. Pharmacol.* 41:404–411.

(Continued)

*Primary Examiner*—Gollamudi S. Kishore
(74) *Attorney, Agent, or Firm*—Morrison & Foerster LLP

(57) ABSTRACT

This invention discloses emulsion formulations comprising an aqueous carrier and the following components: triglyceride, cholesterol, phospholipid, at least one charged lipid, at least one hydrophilic biologically active molecule and, optionally, cholesteryl ester, and/or apoprotein; methods of preparing these emulsions; and the use of these emulsions as vehicles for the delivery of hydrophilic biologically active molecules to cells.

3 Claims, 15 Drawing Sheets

OTHER PUBLICATIONS

Bijsterbosch, M. K. et al, (1994). "Synthesis of the Dioleoyl Derivative of Iododeoxyuridine and its Incorporation into Reconstituted High Density Lipoprotein Particles," *Biochemistry* 33:14073–14080.

Gao, X. et al., (1991). "A Novel Cationic Liposome Reagent for Efficient Transfection of Mammalian Cells," *Biochem. Biophys. Res. Commun.* 179(1):280–285.

Gao et al., (1996). "Potentiation of Cationic Liposome–Mediated Gene Delivery by Polycations," *Biochem.* 35:1027–1036.

Guo, Z. S. et al., (1996). "Evaluation of Promotor Strength for Hepatic Gene Expression in Vivo Following Adenovirus–Mediated Gene Transfer," *Gene Ther.* 3:802–810.

Huettinger, M. et al., (1988). "Characteristics of Chylomicron Remnant Uptake into Rat Liver," *Clin. Biochem.* 21:87–92.

Kaplitt, M. G. et al., (1994). "Long–Term Gene Expression and Phenotypic Correction Using Adeno–associated Virus Vectors in the Mammalian Brain," *Nature Genet.* 8:148–154.

Kay, M. A. et al., (1995). "Therapeutic Serum Concentrations of Human Alpha–1–Antitrypsin after Adenoviral–mediated Gene Transfer into Mouse Hepatocytes," *Hepatology* 21(3):815–819.

Malone et al., (1989). "Cationic Liposome–mediated RNA Transfection," *Proc. Natl. Acad. Sci. USA* 86:6077–6081.

Pinnaduwage et al., (1989). "Use of a Quaternary Ammonium Detergent in Liposome Mediated DNA Transfection of Mouse L–Cells" *Biochim. Biophys. Acta* 985:33–37.

Redgrave, T. G. et al., (1985). "Metabolism of Protein–free Emulsion Models of Chylomicrons in Rats" *Biochem. Biophys. Acta*. 835:104–112.

Reimer, D. L. et al., (1995). "Formation of Novel Hydrophobic Complexes Between Cationic Lipids and Plasmid DNA," *Biochemistry* 34:12877–12883.

Rensen, P. C. N. et al., (1995). "Selective Liver Targeting of Antivirals by Recombinant Chylomicrons–A New Therapeutic Approach to Hepatitis B," *Nature Med.* 1(3):221–225.

Sambrook, J. et al., (1989). *Molecular Cloning: A Laboratory Manual*. Cold Spring Harbor Laboratory Press, Cold Spring Harbor, N. Y., (Table of Contents).

Sautereau, A. M. et al., (1995). "Physico–chemical Characterization of Low Density Lipoprotein Containing a Cytotoxic Drug: The 2N–methyl–9–oleoyl–ellipticinium," *Eur. J. Pharm. Biopharm.* 41(2):136–139.

Shaw, J. M. et al., (1991). "Lipoproteins are Carriers of Pharmacological Agents," Marcel & Dekker, NY, NY, (Table of Contents).

Sternberg et al. (1994). "New Structures in Complex Formation Between DNA and Cationic Liposomes Visualized by Freeze–fracture Electron Microscopy," *FEBS Lett.* 356:361–366.

Zhou et al., (1991). "Lipophilic Polylysines Mediate Efficient DNA Transfection in Mammalian Cells" *Biochim. Biophys. Acta* 1065:8–14.

* cited by examiner

- Naked DNA
- Reconstituted chylomicrons
- Reconstituted chylomicrons without extrusion
- Empty reconstituted chylomicrons containing TC-Chol + Naked DNA
- Empty reconstituted chylomicrons without TC-chol + Naked DNA

EMULSION FORMULATIONS FOR HYDROPHILIC ACTIVE AGENTS

This application is a continuation of Ser. No. 09/214,546, filed on Feb. 17, 1999, now U.S. Pat. No. 6,610,321 which is a 371 of PCT/US97/12544, filed on Jul. 3, 1997 which, is a continuation application of U.S. Ser. No. 08/676,867 filed Jul. 3, 1996, now abandoned the contents of which are hereby incorporated by reference.

FIELD OF INVENTION

This invention relates to emulsions and their use as delivery vehicles for biologically active molecules. In particular, the invention relates to emulsion formulations comprising an aqueous carrier and the following components: triglyceride, cholesterol, phospholipid, charged lipid, hydrophilic biologically active molecule and optionally, cholesteryl ester, and/or apoprotein(s); to methods of preparing these emulsions; and to their uses as vehicles for the delivery of hydrophilic biologically active molecules to cells.

BACKGROUND OF INVENTION

The field of selective delivery of biologically active molecules to specific cellular targets is rapidly advancing. Among the various systems that have been studied for their ability to deliver bioactive molecules to cells, lipoproteins, which form naturally occurring biological emulsions, are considered attractive as delivery vehicles for a number of reasons: 1) as endogenous carriers of cholesterol and other lipids in the blood circulation, they are not immunogenic and escape recognition by the reticuloendothelial system; 2) physicochemical characterization of drug-loaded lipoproteins indicates that particles with the same physicochemical properties as the native lipoproteins can be obtained; 3) lipoproteins are removed from the circulation by specific receptors that recognize their apoproteins or, they may be directed to nonlipoprotein receptors by chemical modification of their apoproteins (see, for example, Bijsterbosch, M. K. and van Berkel, T. J. C. (1990) *Adv. Drug Delivery Revs,* 5:231–251); 4) lipoproteins are physically stable due to their compact, neutral, apolar core; 5) the apolar core of lipoproteins provides an ideal domain for lipophilic molecules since molecules that are transported in the core of the lipoprotein are protected from the environment during transportation and the environment is protected from the molecule; and 6) lipoproteins can be synthesized from commercially available lipids and isolated apoproteins.

Examples of the use of lipoproteins as delivery vehicles for bioactive molecules include U.S. Pat. Nos. 4,868,158 and 5,324,821 which refer to the preparation of lipoproteins modified by incorporation of a lipophilic active substance into their apolar core. However, since many of the biologically active molecules used for treatment and/or prevention of diseases are too hydrophilic for incorporation into the apolar core of lipoproteins, investigators have attempted to find methods which would permit the incorporation of hydrophilic molecules into lipoproteins.

One approach that has been utilized is to couple hydrophilic molecules to hydrophobic anchors in order to render the hydrophilic molecule more lipophilic. For example, van Berkel has reported the synthesis of a dioleoyl derivative of the anti-viral nucleoside analogue iododeoxyuridine and its incorporation into either high density lipoproteins (HDL) (Bijsterbosch, M. K. et al. (1994) *Biochemistry,* 33:14073–14080) or chylomicrons (Rensen, P. C. N. et al. (1995) *Nature Medicine,* 1:221–225). Unfortunately, the use of conjugation to facilitate incorporation of hydrophilic molecules into lipoproteins has a number of potential drawbacks: 1) since the conjugated molecules are typically incorporated into a lipid or a protein residue on the surface of the lipoproteins, the conjugated molecule may interfere with the interaction of the apoprotein of the lipoprotein and its receptor; 2) such surface-modified particles may show a greater tendency to aggregate due to a potential loss of surface charge; 3) attachment of bioactive molecules to the surface of lipoproteins exposes the molecules to the environment and vice versa; 4) "derivatization" of hydrophilic molecules by conjugation to hydrophobic anchors may affect the biological activity of the hydrophilic molecule; and 5) such a "conjugation" approach is impractical for rendering larger molecular weight hydrophilic molecules hydrophobic enough to be incorporated into the apolar core of the lipoproteins.

SUMMARY OF THE INVENTION

The present invention relates to emulsion formulations designed to mimic native (i.e. naturally occurring) lipoprotein emulsions in vivo.

The emulsion formulations of the invention comprise an aqueous carrier and the following components: triglyceride, cholesterol, phospholipid, at lease one charged lipid, at least one hydrophilic biologically active molecule, and optionally, protein(s), and/or cholesteryl ester. By "protein" is meant a protein that targets the emulsion to a specific cell type. A preferred protein is an apoprotein, where the apoprotein may be free of lipid or may be complexed covalently or ionically with lipid to form an apolipoprotein.

In formulating the emulsions of the invention, the charged lipid and hydrophilic biologically active molecule are first mixed together in a charged lipid: bioactive molecule ratio suitable to result in the formation of a hydrophobic charged lipid:bioactive molecule complex (herein "hydrophobic complex") which is soluble in the organic phase of a two phase aqueous-organic system. This hydrophobic complex is then mixed with triglyceride, cholesterol, phospholipid and optionally, cholesteryl ester, and/or apoprotein, to form the emulsions of the invention.

In a preferred embodiment, at least one negatively charged bioactive molecule is mixed together with at least one cationic lipid to form the hydrophobic complex.

In an alternative embodiment at least one positively charged bioactive molecule may be mixed together with at least one anionic lipid to form the hydrophobic complex.

By cationic lipid or anionic lipid is meant a lipid having a net positive (cationic lipid) or net negative (anionic lipid) charge at or near physiological pH.

It is believed that the emulsions of the present invention therefore comprise an apolar core composed of triglycerides and optionally, cholesteryl esters, into which the hydrophobic complex of a hydrophilic bioactive molecule and preferably, a cationic lipid, is incorporated; the apolar core being surrounded by a phospholipid monolayer in which cholesterol and optionally, specific apoprotein(s) are incorporated.

The invention also relates to methods of producing the emulsion formulations of the invention.

In one embodiment, the emulsion formulation of the invention may be produced by:

(a) mixing a hydrophobic complex of hydrophilic bioactive substance and cationic lipid with triglyceride, phospholipid, cholesterol and optionally cholesteryl ester in an organic solvent;

(b) removing the organic solvent to leave a lipid film;

(c) and suspending the film in an aqueous buffer to produce the emulsion.

If the emulsions are not uniform in size, the emulsions may be further purified to remove emulsions of undesired size. Such purification also serves to sterilize the emulsions.

In an alternative embodiment, where the emulsion formulation of the invention is to contain a water-soluble apoprotein, the apoprotein may be added to, and mixed with, the emulsion formed by the suspension of the film in step (c) above.

Of course, when isolated apoproteins such as apo-B-48 and apo-B-100, which are not soluble in aqueous buffer, are to be included in the emulsions, the above method of producing an emulsion containing apoproteins may be modified such that apoprotein is included among the components combined in the organic solvent prior to the film formation.

In an alternative embodiment, the emulsion formulations of the invention may be produced by dissolving the hydrophobic complex of cationic lipid and a hydrophilic bioactive molecule in the apolar core of a reconstituted lipoprotein emulsion.

In one embodiment, such a method comprises:

(a) extracting native lipoprotein, which preferably has been lyophilized, with an organic solvent;

(b) mixing the extracted lipoprotein lipids with a hydrophobic complex of cationic lipid and hydrophilic bioactive molecule in the organic solvent;

(c) removing the organic solvent to leave a lipid film;

(d) adding aqueous carrier to produce the emulsion; and (e) purifying said emulsion, if necessary, to sterilize and obtain emulsions of desired size.

Typically, the emulsion formulations produced by this method would be apoprotein-free emulsions since most apoproteins are water-soluble and would not be contained in the organic solvent extract.

However, as noted above, apoproteins such as β-48 and β-100 are extractable with organic solvent. Therefore, it is understood that in cases where the lipoprotein to be extracted in step (a) is, for example, LDL, the organic extract to be mixed with hydrophobic complex in step (b) would contain apo-B-100 as well as the lipoprotein lipids. Of course, it is understood that even if the lipoprotein selected to be extracted by organic solvent does not contain apoprotein soluble in organic solvent, water-soluble apoprotein can be added to the aqueous suspension produced in step (d) in the above method to produce an apoprotein-containing emulsion.

In yet another embodiment, the emulsions of the invention may be produced by preparing the hydrophobic complex of cationic lipid and hydrophilic biologically active molecule as a dry film (i.e. by removal of the organic solvent into which the hydrophobic complex partitions), then adding native lipoproteins to the dry film and vortexing, such that the hydrophobic complex contained in the dry film rehydrates and partitions into the apolar core of the lipoprotein.

The invention therefore also relates to a lipid film capable of forming the emulsion formulations of the present invention upon suspension in an aqueous carrier. The film comprises triglyceride, cholesterol, phospholipid, cationic lipid, hydrophilic biologically active molecule and optionally, cholesteryl ester and/or water-insoluble apoproteins. Where the film comprises apoprotein, it is designated a lipid protein film.

The invention also relates to methods for delivering hydrophilic bioactive molecules to cells in vitro or in vivo.

In one embodiment, the method of delivering hydrophilic biologically active molecules to cells in vivo comprises administering to an animal an effective amount of an emulsion formulation of the present invention. Preferred animals are humans. Thus, for example, where the bioactive molecule is a gene or an oligonucleotide, the invention relates to the use of the emulsion formulations in gene or oligonucleotide therapies respectively.

DETAILED DESCRIPTION OF THE INVENTION

Figure 1A:
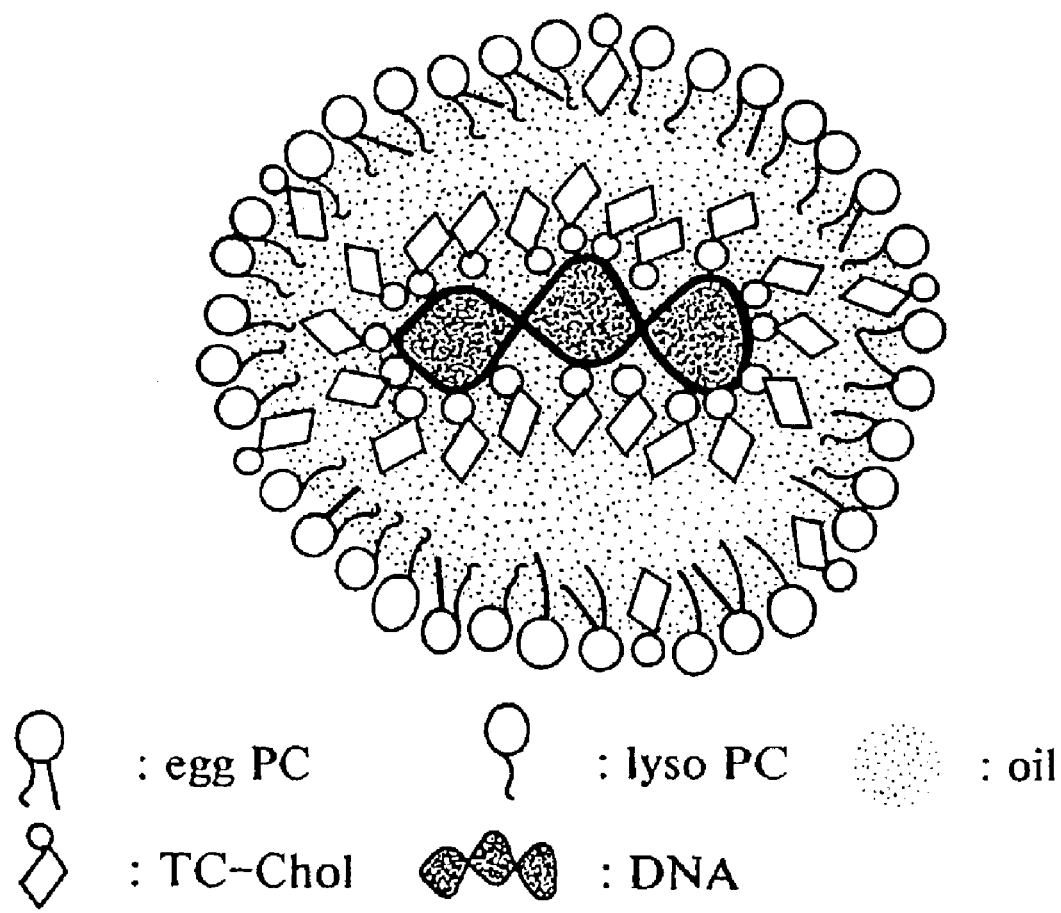
FIGS. 1A and 1B are cartoons showing proposed structures of an emulsion of the invention in which the hydrophobic DNA:TC-chol complex is incorporated into the apolar core of the emulsion.
Figure 1B:
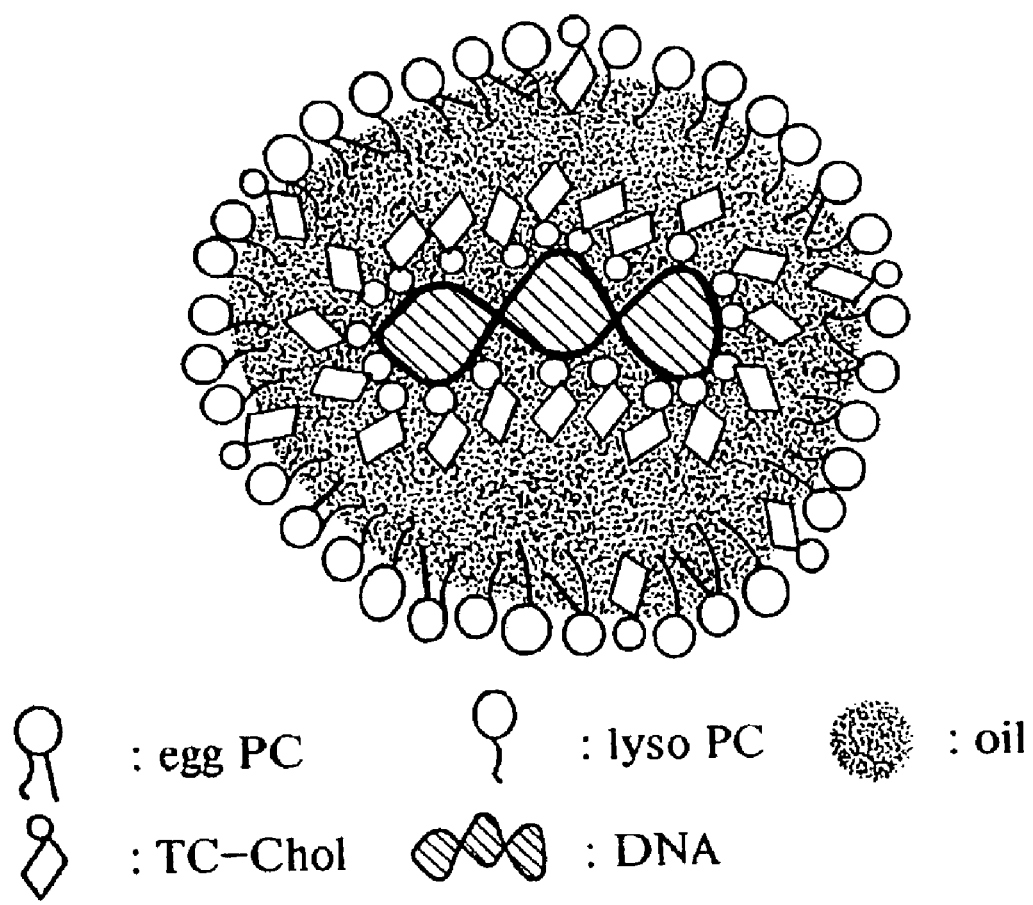

This invention relates to emulsion formulations designed to mimic native lipoprotein emulsions in vivo and to the in use as vehicles for the delivery to cells of hydrophilic biologically active molecules.

In particular, the emulsion formulations of the invention comprise an aqueous carrier and the following components: triglyceride, cholesterol, phospholipid, at least one charged lipid which is preferably a cationic lipid, at least one hydrophilic biologically active molecule and optionally, cholesteryl ester and/or apoprotein. It is contemplated that the inclusion of apoproteins in the emulsion formulations of the inventions is optional since apoprotein-free emulsions have been demonstrated to complex with the appropriate apoproteins in the circulation (Redgrave, T. G. and Maranhao, R. C. (1985) *Biochem. Biophys. Acta.*, 835:104–112) and still target to receptor-bearing cells.

To produce the emulsions of the invention, the charged lipid, which is preferably a cationic lipid, and a hydrophobic biologically active molecule, which is preferably negatively charged, are first mixed together to form a hydrophobic complex which is soluble in the organic phase of a two phase system. This hydrophobic complex is then mixed with other lipid components which include triglycerides, cholesterol, phospholipid, and optionally cholesteryl ester. Apoprotein(s) may also optionally be combined with the other lipids to produce the emulsion formulations of the invention.

The hydrophobic complexes to be mixed with the other lipid components and optionally, apoprotein, to produce the emulsion formulations of the invention, are produced by mixing charged lipid and hydrophilic bioactive molecule in a ratio that produces a complex soluble in an organic solvent such as chloroform.

It is understood that since the extraction efficiency approaches 100% when the charge ratio of cationic lipid to negatively charged bioactive molecule is about 1.0, the amount of cationic lipid to be mixed with a hydrophilic bioactive substance to form a hydrophobic complex may be readily determined by titrating increasing amounts of cationic lipid against a fixed amount of bioactive molecule at an appropriate pH and measuring the partitioning of the resultant complex into the organic phase of a two phase system. The pH and ionic strength of the system should be sufficiently controlled to allow for complex formation between the biologically active molecule and the charged lipid. Aqueous phases having low ionic strength are preferred.

Thus, water is preferred over saline. Methods for measuring partitioning of the hydrophobic complex of cationic lipid and hydrophilic biologically active molecule into the organic phase include, but are not limited to, radiolabelling of the bioactive molecule as described in Example 1.

Cationic lipids suitable for complexing with hydrophilic bioactive molecules to produce a hydrophobic complex are any cationic lipid, or mixture of cationic lipids, which is capable of forming a complex that partitions into the organic phase of a two-phase aqueous/organic system. It is therefore contemplated that both monovalent and polyvalent cationic lipids may be utilized to form hydrophobic complexes with bioactive molecules. Preferred cationic lipids for use in forming the complexes of the invention include, but are not limited to, TC-Chol, and those cationic lipids referred to in Reimer et al. (*Biochemistry* (1995) 34:12877–12883) such as dimethyldioctadecylaminonium bromide (DDAB), dioleyldimethylammonium chloride (DODAC), 1,2-dioleoyl-3-N,N,N-trimethylaminopropane chloride (DOTMA) 2,3-dioleoyloxy-N-[2-(spermidine carboxyamido) ethyl]-N, N-dimethyl-1-propaninium trifluoroacetate (DOSPA), diheptadecylamidoglycylspermidine (DHGS) and 1,2 bis (oleoyloxy)-3-(trimethylammonio) propane (DOTAP).

Preferred nmol/μg ratios of cationic lipid to bioactive molecule are those that result in recovery of at least 90% of the bioactive molecule in the organic phase, more preferably greater than 95% recovery in the organic and most preferably 100% recovery in the organic phase.

Examples of hydrophilic biologically active molecules which may be complexed with cationic lipid to form hydrophobic complexes include, but are not limited to, nucleic acids such as DNA, cDNA, RNA (full length mRNA, ribozymes, antisense RNA, decoys), oligodeoxynucleotides (phosphodiesters, phosphothioates, phosphoramidites, and all other chemical modifications), oligonucleotide (phosphodiesters, etc.) or linear and closed circular plasmid DNA; carbohydrates; proteins and peptides, including recombinant proteins such as for example cytokines (eg interleukins), trophic and growth or naturation factors (eg NGF, G-CSF, GM-CSF), enzymes, vaccines (eg HBsAg, gp120); and hydrophilic drugs. It is contemplated that when hydrophilic biologically active molecules are to be complexed with cationic lipid, one or more of the different bioactive molecules recited above may be included in the hydrophobic complex (eg, antisense oligonucleotides to two different genes).

Since the hydrophilic substance is believed to form a hydrophobic complex with the charged lipid based on charge interaction and the preferred charged lipid is a cationic lipid, preferred hydrophilic biologically active molecules are negatively charged molecules such as nucleic acids, negatively charged proteins and carbohydrates including polysaccharides, or negatively charged drugs.

In a more preferred embodiment the biologically active molecules are nucleic acids and in a most preferred embodiment, the nucleic acids are nucleic acids which encode a gene or a gene fragment or which effect transcription and/or translation.

Of course, it is understood that positively charged hydrophilic biologically active molecules could also be readily formulated into the emulsions of the invention by mixing the positively charged biologically active molecule with an anionic lipid to produce a hydrophobic complex which is soluble in organic solvent. As with the hydrophobic complex of cationic lipid and negatively charged bioactive molecule, the hydrophobic complex between anionic lipid and positively charged bioactive molecule could then be mixed with triglycerides, cholesterol, phospholipid and optionally, cholesteryl ester and/or apoprotein(s) to produce the emulsions of the invention.

Suitable anionic lipids for complexing with a positively charged hydrophobic bioactive molecule to produce a hydrophobic complex are any anionic lipid, or mixture of anionic lipids, which are capable of forming a complex that partitions into the organic phase of a two-phase aqueoused/organic system. Examples of such anionic lipids include, but are not limited to, phosphatidyl glycerol, phosphatidic acid or a similar phospholipid analog.

The other lipid components, triglyceride, cholesterol, phospholipid and optionally, cholesteryl ester, which may be mixed with the hydrophobic complex to produce the emulsion formulations of the invention are those found in the four major classes of lipoproteins: chylomicron, very low density lipoproteins, (VLDL), low density lipoproteins (LDL) and high density lipoproteins (HDL).

Triglycerides which may be used to formulate the emulsions of the present invention include purified triglycerides of varying fatty acid composition or vegetable oils which contain as their major component, triglycerides of various fatty acid compositions. Preferred sources of triglycerides are animal and vegetable oils, in particular, oils which have been shown to be suitable for use in vivo such as soya bean oil, olive oil, cottonseed oil, sesame oil, and cod liver oil. Such oils may be used alone or in combination with other oils as a source of triglycerides. For example, olive oil and sesame oil may be used to formulate a single emulsion. A preferred oil is olive oil.

Phospholipid utilized to formulate the emulsion may be a single phospholipid species or a mixture of phospholipid species. Examples of phospholipids include, but are not limited to, phosphatidylcholine (PC), or phosphatidylethanolamine (PE), lyso PC or lyso PE, or fully saturated or partially hydrogenated PC or PE having aliphatic chains between about 6 and about 24 atoms in length.

By cholesteryl esters is meant cholesteryl esters containing saturated and unsaturated fatty acids of between about 10 and about 24 carbons in length esterified to the three carbon of cholesterol. Preferred cholesteryl esters are esters of unsaturated fatty acids between 16 and 18 carbon atoms in length such as oleic acid. It is contemplated that a single species of cholesteryl ester or multiple species of cholesteryl ester may be used in formulating an emulsion formulation of the invention.

When apoproteins are to be included in the emulsion of the invention, one or more of the different apoproteins may be selected from any of the apoproteins shown in Table 1.

TABLE 1

| Lipoprotein | Chylomicrons | VLDL | LDL | HDL |
|---|---|---|---|---|
| Major apoproteins | AI, AIV, B-48, CI, CII, CIII, E | B-100, CI, CII, CIII, E | B-100 | AI, AII, E |

The apoproteins to be utilized in the present invention may be isolated from native lipoproteins by known methods such as extraction of lipoproteins with organic solvent or detergents or they may be recombinantly expressed (examples of apoproteins which have been cloned include E, B-100 and AI) and then purified by methods known to those of ordinary skill in the art. Since it is contemplated that the addition of apoprotein to the emulsion formulation may produce an emulsion which demonstrates enhanced efficiency and specificity of delivery of the bioactive substance due to efficient receptor-mediated uptake of the apoprotein-containing emulsion formulation, preferred apoproteins to be included in the emulsions of the invention are those that are involved in receptor-mediated catabolism such as apo B-100 and apo E. For example, reconstituted chylomicrons appear to be taken up by hepatocytes via apolipoprotein E-specific receptors (Huettinger, M. et al., *Clin. Biochem.,* 21, 87–92 (1988); Rensen, P. C. N. et al. *B. Nat. Med.,* 1, 221–225 (1995)).

It is further contemplated that when apoproteins are included in the emulsion formulations of the invention, the apoproteins may be modified to direct the emulsion formulation to non-lipoprotein receptors. For example, reductive lactosamination of LDL and HDL has been demonstrated to direct these lipoproteins to galactose receptors present on Kupfer cells and liver parenchymal cells (Bijsterborch, M. K. and van Berkel, Th. J. C. (1992) *Anol. Pharmacol.* 41:404–411) and acetylation of LDL directs that lipoprotein to macrophages, monocytes and endothelial cells (Shaw, J. M. (1991), et al., Lipoproteins are Carriers of Pharmacological Agents", Marcel & Dekker, New York, N.Y.)

In addition, the apoproteins may be chemically modified with, for example, monoclonal antibodies exhibiting specificity towards cell-surface components, in order to broaden the range of cellular specificities of the emulsion formulations of the invention. (see Shaw, J. M. ed. (1991) "Lipoproteins as Carriers of Pharmaceutical Agent"; Marcel Dekker Inc. New York, N.Y.).

The weight ratios of triglyceride, cholesterol and phosphblipid and optionally cholesteryl ester, to be mixed with the hydrophobic complex to form the emulsions of the invention may be selected from the ranges of the weight percentages of these four lipid components known to be found in chylomicrons, VLDL, LDL and-HDL as shown below in Table 2.

TABLE 2

| Lipoprotein | Chyomicrons | VLDL | LDL | HDL |
|---|---|---|---|---|
| Phospholipids (%) | 3–6 | 15–20 | 18–24 | 26–32 |
| Cholesterol (%) | 1–3 | 4–8 | 6–8 | 3–5 |
| Cholesteryl esters (%) | 2–4 | 16–22 | 45–50 | 15–20 |
| Triglycerides (%) | 80–95 | 45–65 | 4–8 | 2–7 |

Thus, the dry weight % of phospholipids may range from about 3% to about 32%, the weight % of cholesterol may range from about 1% to about 8%, the weight % of cholesteryl esters may range from about 0% to about 50% and the weight % of triglycerides may range from about 2% to be about 95%. More preferred ranges are phospholipids, 20–30%, cholesterol, 1–4%; triglycerides, 30–80%; and cholesteryl esters, 2–20%. Most preferred percentages are phospholipids, 25%; cholesterol, 2%, triglycerides, 70% and cholesteryl esters, 3%. The dry weight % of phospholipids, triglycerides, cholesterol and optionally cholesteryl esters given above are the dry weight %s to be mixed with the hydrophobic complex to produce the emulsions of the invention. These weight %s are believed to be similar to the weight %s of these lipids present in the resultant emulsion.

When mixed with the other lipid components (triglyceride, cholesterol, cholesteryl ester, phospholipid), the weight % of apoprotein as a % of the combined dry weight for the other lipids may range from about 1–2% to up to about 45–55%.

The amount of hydrophobic complex to mix with the other lipid components, and optionally apoprotein, to produce the emulsions of the invention is determined by the ratio of the weight of bioactive molecule in the hydrophobic complex to the total weight of the other lipid components. A preferred weight ratio of bioactive substance to other lipid components (cholesterol, triglycerides, cholesteryl ester, and phospholipid) in the emulsion of the invention is preferably from about 1:50 to about 1:400, more preferably 1:100 to about 1:300 and most preferably from about 1:150 to about 1:250.

The present invention therefore relates to methods for making the emulsion formulations of the present invention.

In one embodiment, the method comprises:

(a) mixing the hydrophobic complex of cationic lipid and hydrophilic bioactive molecule in an organic solvent with triglycerides;

(b) removing the solvent to leave a lipid film;

(c) suspending the lipid film in an aqueous carrier to form the emulsion; and (d) purifying the emulsion, if necessary to sterilize and obtain emulsions.

Where the emulsion of the invention is to contain a water-soluble apoprotein, the apoprotein may be added to, and mixed with, the emulsion formed by resuspension of the film.

Where water-insoluble apoproteins such as apo β-48 and apo β-100 are to be included in the emulsions of the invention, the emulsions are produced by including the water-insoluble apoprotein among the components combined in the organic solvent prior to the film formation.

In addition to being made from commercially available lipids and optionally, isolated apoproteins, the emulsion formulations of the invention may be produced by extracting native lipoproteins with, for example, organic solvents or detergents, and then reconstituting the components (lipids and optionally, apoprotein) extracted from the lipoprotein in the presence of the hydrophobic complex.

In one embodiment, an emulsion produced by this approach is generated by:

(a) extracting native lipoprotein, which has preferably been lyophilized, with an organic solvent;

(b) incubating the extracted lipoprotein lipids with the hydrophobic complex of cationic lipid and hydrophilic bioactive molecule;

(c) removing the solvent to leave a lipid film;

(d) suspending the lipid film in an aqueous carrier to produce the emulsion; and (e) purifying the emulsion, if necessary to obtain emulsions of defined size and to sterilize the emulsion.

In this embodiment, the lipoprotein, which is extracted with organic solvent, is a native lipoprotein such as chylomicron, VLDL, LDL or HDL isolated from sera by methods known in the art such as density-gradient centrifugation, gel filtration, agarose gel electrophoresis or plasmapheresis. Since most apoproteins found in native lipoproteins are not extractable with organic solvent, most of the emulsions produced by the above method will be apoprotein-free emulsions unless 1) water-soluble apoprotein (either from the native lipoprotein or recombinantly produced) is added to the aqueous suspension produced in step (d) or 2) the lipoprotein contains an apoprotein which is extractable with organic solvent (eg. apo B-100 in LDL) such that the organic extract mixed with hydrophobic complex in step (b) will contain both lipoprotein lipids and organic-extractable (lipid-soluble) apoprotein.

The organic solvent used in the above methods may be any organic solvent which does not leave a toxic residue following removal and which solubilizes the lipid components of the emulsion. Examples of suitable solvents include lower alcohols, dimethoxyethane, dioxane, tetrahydrofuran, tetrahydropyran, diethylether, acetone, dimethylsulfoxide (DMSO), dimethylformamides (DMF), and halogenated hydrocarbons, such as chloroform, acetonitrile, or mixtures thereof. A preferred organic solvent is chloroform.

The organic solvent may be removed in the above methods under a suitable gas such as argon or nitrogen and/or under a vacuum. The dried film may then be lyophilized and stored at about −80 to about 37° C. or may be resuspended in a suitable aqueous carrier. It is also contemplated that after the film is resuspended in an aqueous carrier, the resultant emulsion may be lyophilized and stored at about −80° C. to about 37° C.

Aqueous carriers suitable for use in this invention are non-toxic to cells and may or may not be buffered. When the carriers are buffered, suitable buffers include buffers such as citrate, carbonate, bicarbonate, acetate, Tris, glycinate and maleate. Aqueous carriers which may be used in the formulations of this invention include, but are not limited to, distilled water, normal saline solution and phosphate-buffered saline. It is understood that the aqueous carrier in which the film is suspended may include ingredients such as stabilizers, antibiotics, or antifungal and antimycotic agents.

"Purification" of the emulsions of the invention, where desired, may be carried out by density gradient centrifugation, gel filtration, FPLC or HPLC, or extrusion through membranes of a particular pore size. This purification step is preferred in the production of the emulsion formulations of the invention because it reduces the size of the emulsions to a uniform, small size by removing aggregates and it also serves to sterilize the emulsions.

Since the permeability of capillary endothelium to lipoproteins is known to vary widely among different tissues and may affect the rate of uptake by certain organs, the emulsions of the invention are preferably small enough to penetrate the smallest diameter fenestrations of endothelial cells. In a preferred embodiment, the average diameter of the emulsions of the invention is about 500 nm, more preferably about 200 nm and most preferably about 100 nm. It is contemplated that by altering the ratios of the various lipid components to mimic those found in more dense lipoproteins such as LDL or HDL or, by increasing the dry weight % of phospholipid, relative to the combined dry weight % of triglyceride, cholesterol and optionally cholesteryl ester, the diameter of the emulsion of the invention may be reduced.

The emulsions of the present invention may be utilized to deliver hydrophilic biologically active substances to cells in vitro or in vivo.

When the biologically active molecule is an antigenic protein or peptide, the emulsion formulations of the present invention may be utilized-as vaccines.

In another embodiment, where the biologically active molecule is a polynucleotide such as a gene (a nucleic acid molecule comprising expression control sequences operatively linked to a nucleic acid sequence encoding a protein or peptide), it is contemplated that the emulsion formulations of the invention may be utilized to deliver genes to cells to treat or prevent disease. For example, the emulsions and methods of this invention may be used to deliver genes to hepatocytes to treat acquired diseases such as viral hepatitis infection (eg hepatitis B and C), cancer and alcoholic cirrhosis or to treat inherited diseases such as alpha 1-antitrypsin deficiency, familial hypercholesterolemia hemophilia A, tyrosinemia or phenylketonuria; to vascular endothelial cells to treat acquired diseases such as atherosclerosis and to reticuloendothelial cells to treat acquired diseases such as leishmaniasis.

In an alternative embodiment, where the polynucleotide is an oligonucleotide, the emulsion formulations may be used to treat acquired diseases such as viral infection or cancer.

Although the data presented herein demonstrates a high level of transgene expression when an emulsion resembling a chylomicron is used as the delivery vehicle, it is contemplated that since the receptors of other lipoproteins such as LDL and HDL are widespread among many cell-types, emulsions which mimic these lipoproteins in vivo may also be an efficient vehicle for delivery of hydrophobic bioactive molecules to target tissues other than the liver. Those of ordinary skill in the art will readily understand that the emulsion formulations of the invention may therefore be used to specifically deliver hydrophilic bioactive molecules to cells which express receptors specific for the apoprotein or other targeting protein(s) contained in the emulsion formulation as formulated or which is incorporated into the emulsion in vivo. For example, since the LDL receptor is found in cells such as hepatocytes, fibroblasts and endothelial cells, bioactive molecules could readily be delivered to these cells by emulsion formulations containing the apoprotein found in LDL.

Suitable routes of administration of the emulsion formulations of the invention to an animal include inoculation or injection by, for example, intravenous, oral, intraperitoneal, intramuscular, subcutaneous, intra-aural, intraarticular or intra-mammary routes, topical application, for example on the skin, scalp, ears or eyes and by absorption through epithelial or mucocutaneous linings, for example, nasal, oral, vaginal, rectal and gastrointestinal among others, and as an aerosol. Those of ordinary skill in the art would readily understand that the mode of administration may determine the sites in the organism to which the biologically active substance will be delivered and may effect the amount of the formulation to be administered.

All articles or patents referenced herein are hereby incorporated by reference. The following examples illustrate various aspects of the invention but are in no way intended to limit the scope thereof.

EXAMPLES

Materials and Methods

Materials

Cholesterol (Chol), cholesteryl oleate (Chololeate), L-α-lysophosphatidylcholine (Lyso PC), olive oil and dimethyl-dioctadecylammonium bromide (DDAB) were obtained from Sigma. L-α-Phosphatidylcholine (PC) were from Avanti Polar Lipid, luciferase from Calbiochem and 5-bromo-4-chloro-3-indoyl-β-D-galactoside (X-Gal) from Gibco BRL. Luciferase assay system and Coomassie Plus Protein Assay Reagent were from Promega and Pierce, respectively. Calibrator 4 as a standard for hAAT and goat anti-hAAT were purchased from Incstar and Vectastain ABC kit was from Vector.

Plasmids

Plasmids pCMVL and pCMVLacZ contain a fire fly luciferase gene and a bacterial β-galactosidase (β-Gal) gene, respectively, and both of them are driven by a human cytomegalovirus immediate early promoter. pRSVhAAT (Guo, Z. S. et al. (1996) *Gene Therapy* 3:802–810) contains a HAAT gene driven by Raus sarcoma virus promoter. pAAVCMVhAAT was reconstructed from pAAVlac.26

(Kaplitt, M. G. et al. (1994) *Nature Genetics* 8:148–154) and pRSVhAAT as follows: pAAVlac.26 was digested with XbaI followed by ligation with double stranded oligodeoxynucleotide (5'-CTAGACTCGAGT-3') to insert a XhoI site. After digestion of both plasmids by HindIII and XhoI, the 4510 bp fragment from pAAVlac.26 and the 1680 bp fragment from pRSVhAAT were isolated and ligated together. The resulting pAAVCMVhAAT contains two AAV inverted terminal repeat (ITR) sequences flanking the hAAT gene driven by the CMV promoter. These plasmids were amplified in DH5α strain of *E. coli*, isolated by alkaline lysis and purified by cesium chloride gradient centrifugation (Sambrook, J. et al. (1989) Molecular Cloning: A Laboratory manual (Cold Spring Harbor Laboratory Press, Cold Spring Harbor, N.Y.).

Synthesis of Cationic Derivatives of Cholesterol

3-β-[N-(N', N'-dimethylethane)-carbamoyl]cholesterol (DC-Chol), a tertiary ammonium derivative of Chol, was synthesized as described previously (Goo, X. and Huang, L. (1991) *Biochem Biophys Res Commun.* 179:280–285).

3-β-[N(N',N',N'-trimethylethane)carbamoyl]cholesterol (TC-Chol), a quaternary ammonium derivative of Chol, was synthesized by methylation of DC-Chol with iodomethane.

Intraportal Injection

For Examples 4–7

Six week old female CD1 mice were anesthetized via inhalation of dimethyl ether and intramuscular injection of 1 mg of ketamine-HCl and then treated as follows: the livers of mice exposed through a ventral midline incision were injected over 30 seconds into the portal vein using a ½ inch needle with 30 gauge and 1 ml syringe with various amounts of emulsion formulation dissolved in 1 ml isotonic mannitol solution.

For Examples 4A, 6A, 7A 7B and 8

Six weeks old female CD1 mice were anesthetized with intramuscular injection of ketamine hydrochloride (1 mg/20 g of body weight). After the liver was exposed through a ventral midline incision, various amounts of DNA/TC-Chol-emulsion which was dispersed in 1 ml of 5.2% (isotonic) mannitol, were injected into the portal vein using a ½ inch 30 gauge needle and 1 ml syringe.

X-Gal staining. Forty-eight hours after injection, the liver was perfused in situ with 5 ml of 1.25 mM EGTA in PBS (pH 7.5) to remove the blood. The liver was dissected, cut into small blocks and frozen in OCT embedding compound (Miles Scientific). Cryosections of 10 μm in thickness were sampled and placed on polylysine-coated glass slides. Following fixation with 2% glutaraldehyde in PBS containing 0.04 % Nonidet P-40, the liver sections were incubated in a staining solution (0.08% 5-bromo4-chloro-3-indolyl-β-D-galactoside (X-Gal), 5 mM each of $K_3Fe(CN)_6$ and $K_4Fe(CN)_6$ and 2 mM $MgCl_2$ in PBS) at 37° C. for 24 h. The sections were then rinsed three times with PBS and lightly counter stained with hematoxylin.

ELISA for hAAT. ELISA method for measuring blood level of hATT was modified from a published procedure (Kay, M. A. et al. (1995) *Hepatology* 21:815–819), except that an ABC kit containing avidin and biotinylated peroxidase was used.

Example 1

Solubilization of DNA in the Organic Phase

Since chylomicrons are emulsions containing no aqueous phase, native DNA cannot be incorporated into them. Accordingly, experiments were undertaken to "modify" the native DNA such that it would be hydrophobic and therefore be able to be incorporated into the chylomicron.

Four microgram of plasmid pCMVL DNA (plasmid pCMVL contains a luciferase gene driven by the human cytomegalovirus immediate early promoter) containing trace amounts of $^{125}$I-labeled DNA was incubated with various nmol amount of 3β[N-(N',N'-dimethylaminoethane)-carbamoyl]cholesterol (DC-chol), DC-Chol:HCl, 3β[N', N', N'-trimethylaminoethane)-carbamoyl]cholesterol iodide (TC-chol) or dimethyldioctadecylammonium bromide (DDAB) in 410 μl of Bligh and Dyer monophase (chloroform:methanol:water=1:2.1:1, volume ratio) at room temperature for 30 minutes. Subsequently, the monophase was partitioned into a two-phase system by the addition of 100 μl each of chloroform and water. The sample was then mixed by vortexing, and the separation of the upper aqueous and lower organic phases was facilitated by centrifugation at 600×g for 5 minutes at room temperature. Two hundred microliters of the aqueous phase and 100 μl of organic phase were collected separately and their radioactivities were measured using a γ-counter. Radioactivity of the interface was calculated by subtracting the radioactivity of the aqueous and organic phases from the total radioactivity.

Figure 2A:
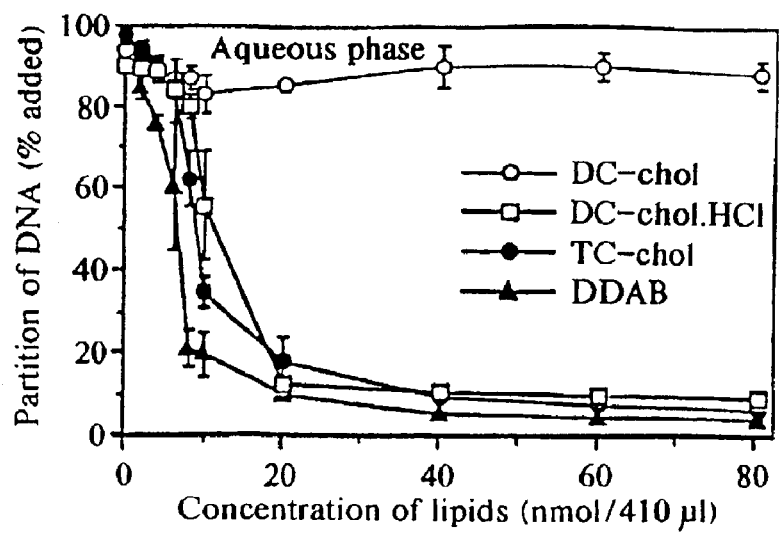
FIG. 2 shows the effect of various cationic lipids on the partitioning of $^{125}$I-labelled DNA into the aqueous phase (top panel), organic phase (middle panel) or interfase (bottom panel) of a two phase system.
Figure 2B:
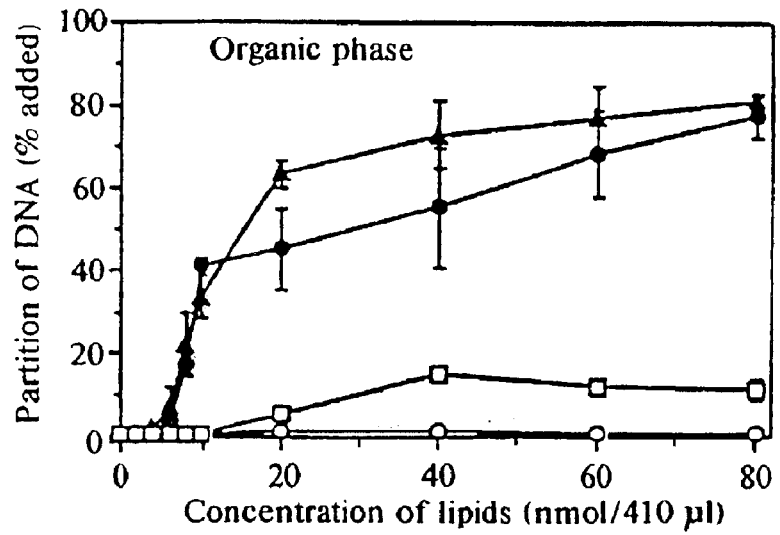
Figure 2C:
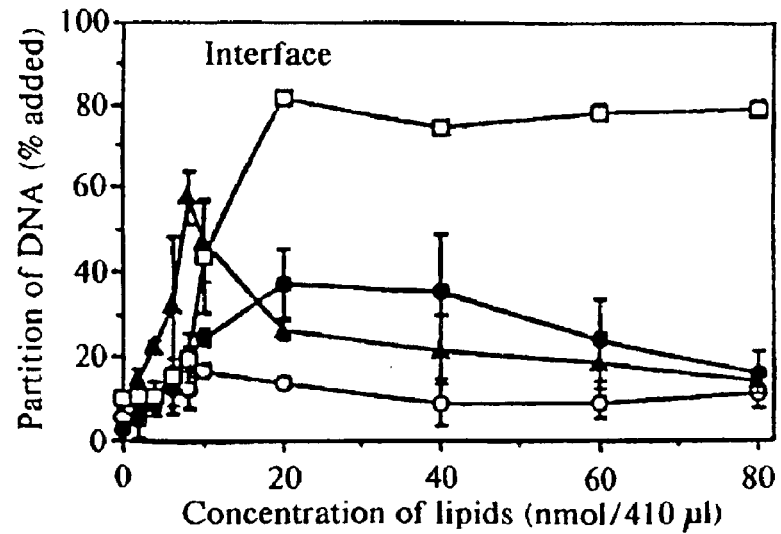

As shown in FIG. 2, DC-chol did not change the solubility of DNA in the aqueous phase. It is believed this failure of DC-Chol to change the solubility of the DNA might be due to the cationic charge of DC-Chol not being strong enough to form a hydrophobic complex with DNA, perhaps due to incomplete ionization of DC-chol in the monophase.

In addition, while the solubility of DNA in the aqueous phase was drastically decreased in the case of the hydrochloric acid salt of DC-chol, the resulting hydrophobic complex was not soluble in the organic phase but stayed at the interface.

However, when a quaternary ammonium derivative of DC-Chol, TC-Chol, was used to form a hydrophobic complex with DNA, it was observed that formation of hydrophobic complex in the interface was saturated at 20 nmoles of TC-chol (ie a ratio of cationic charge of TC-chol to anionic charge of DNA of about 1.8). Moreover, at concentrations of TC-Chol greater than 20 nmol, the complex in the interface was quantitatively transferred to the organic phase thereby suggesting that TC-Chol could form a hydrophobic complex with DNA that could be incorporated into emulsions. The results obtained with TC-chol were almost the same as that obtained from another cationic lipid having a quaternary amine, dimethyldioctadecyl-ammonium bromide (DDAB) (FIG. 2).

Example 1A

Figure 11A:
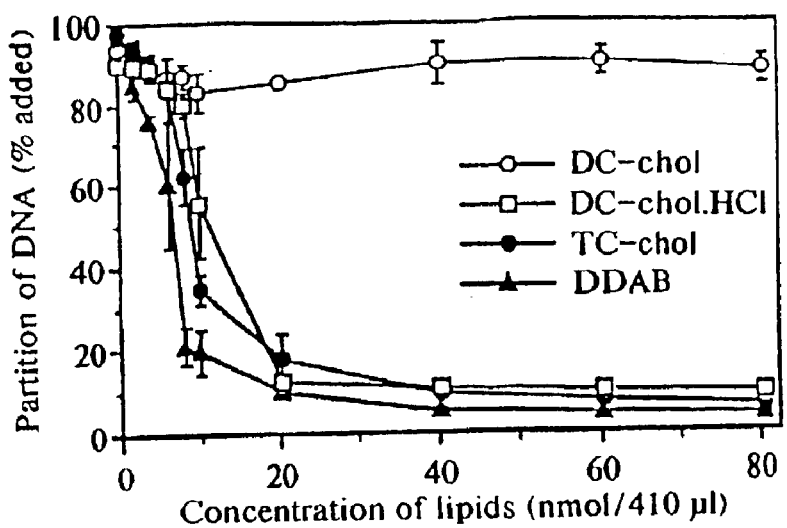
FIGS. 11A–11C show the effect of cationic lipids on the partition of DNA into organic phase. $^{125}$I-DNA (4 µg) was incubated with indicated amounts of cationic lipids in the Bligh and Dyer monophase (410 µl) at room temperature for 30 minutes. The monophase was separated into two phases by the addition of chloroform and water (100 µl each). Partition of DNA into the aqueous phase (FIG. 11A) and organic phase (FIG. 11B) were determined by measuring their radioactivities. Partition of DNA into the interface (FIG. 11C) was determined by subtracting the amount of DNA in the aqueous and organic phases from total DNA added. Each point presents the mean from three experiments ±s.d.
Figure 11B:
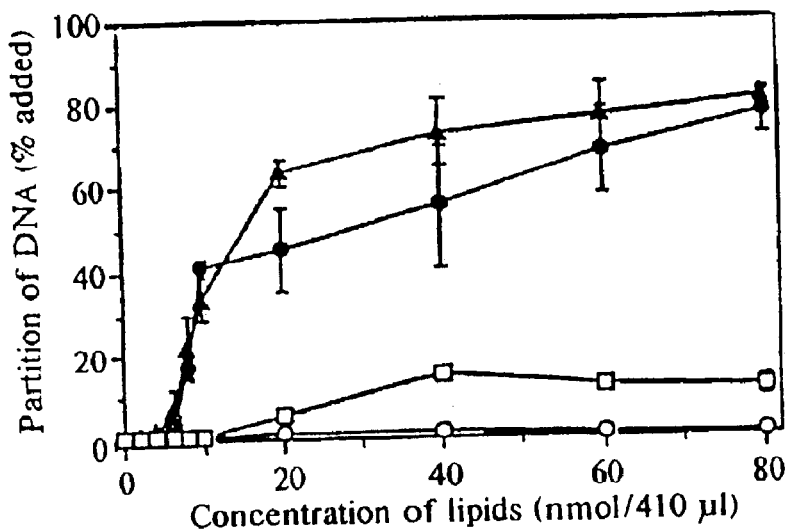
Figure 11C:
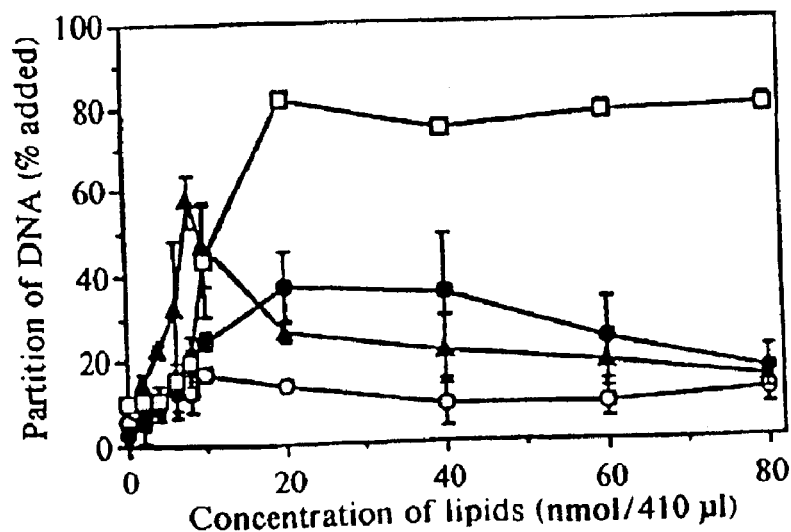

Four μg of plasmid DNA containing trace amount of $^{125}$I-labeled DNA was incubated with various amount of cationic lipids in 410 μl of Bligh and Dyer monophase (chloroform: methanol: water=1:2.1:1) at room temperature for 30 min. Subsequently, the monophase was partitioned into a two-phase system by the addition of 100 μl each of chloroform and water. The sample was mixed by vortexing, and the separation of the upper aqueous and lower organic phases was facilitated by centrifugation at 2,000×g for 10 min at room temperature. Two hundred μl of the aqueous phase and 100 μl of the organic phase were collected separately and their radioactivities were measured using a gamma-counter (Gamma 5500B, Beckman). Radioactivity in the interface was calculated by subtracting the radioactivities of aqueous and organic phases from the total radioactivity. As shown in FIG. 11A, the DC-Chol did not increase the solubility of DNA in the organic phase. Further, although DC-Chol hydrochloride, a salt form of DC-Chol, drastically decreased the solubility of DNA in the aqueous phase, the resulting hydrophobic complex was not soluble in the organic phase (FIG. 11B), but stayed at the interface (FIG. 11C). TC-Chol, a quaternary ammonium derivative of DC-Chol, formed a hydrophobic complex with DNA which is extractable with chloroform (FIG. 11B). At lower concentrations of TC-Chol, the amount of hydrophobic complex in the interface increased and reached the maximum level at 10 nmol of TC-Chol at which the ratio of cationic charge of TC-Chol to anionic charge of DNA was about 1 (FIG. 11C). After that, the complex in the interface (FIG. 1C) was quantitatively transferred to the organic phase (FIG. 11B). The results with TC-Chol were almost the same as that obtained with DDAB, a cationic lipid having a quaternary amine head group.

Example 2

Figure 3:
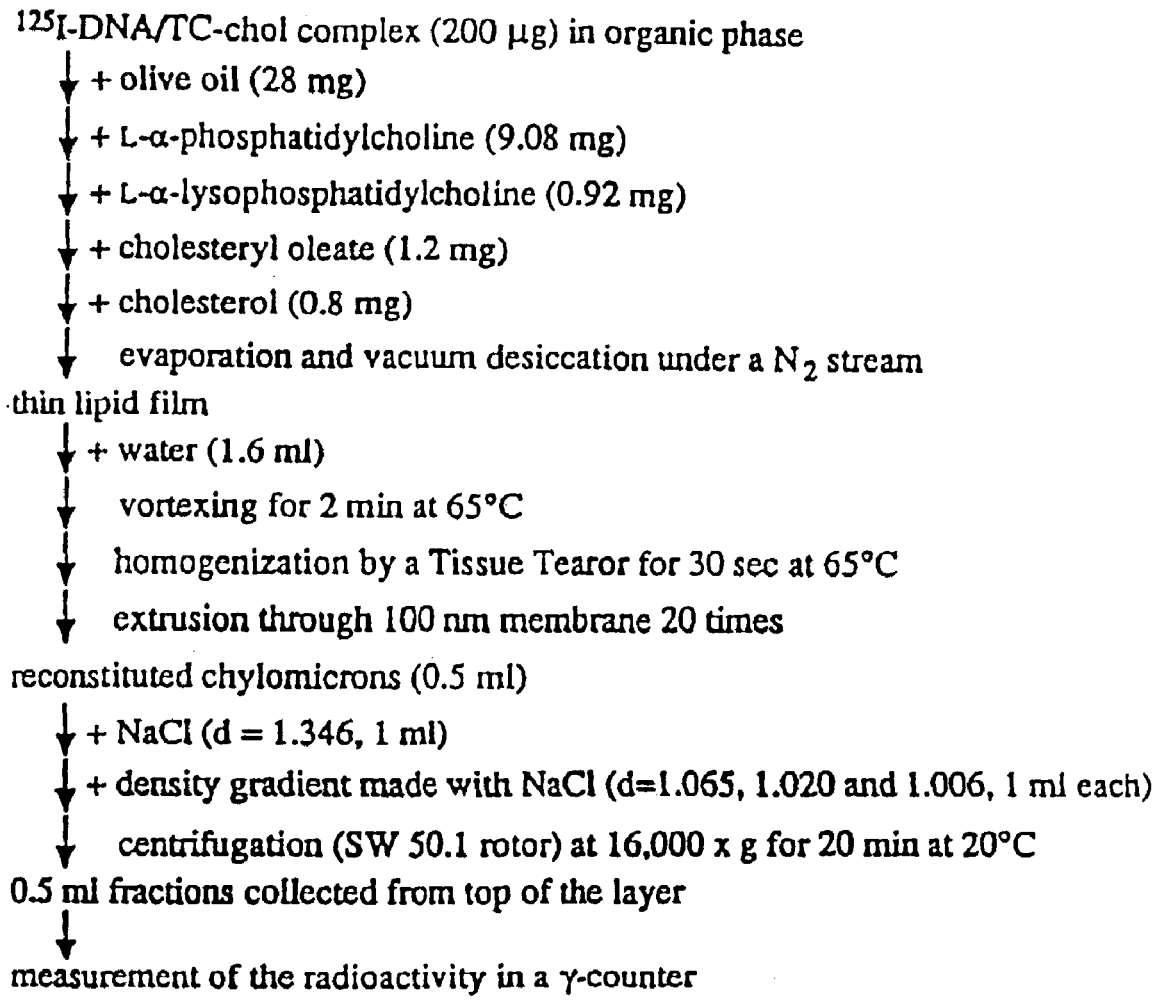
FIG. 3 is a schematic showing the protocol for production of an emulsion of the invention by mixing a hydrophobic complex of DNA/3β[N', N', N'-trimethylaminoethane)-carbamoyl] cholesterol iodide (TC-chol) with olive oil, phosphatidylcholine, lysophosphatidylcholine, cholesteryl oleate and cholesterol.

Production of Emulsions by Mixing Hydrophobic PCMVL DNA/TC-Chol Complex with Olive Oil, Phosphatidylcholine, Lysophosphatidylcholine, Cholesteryl Oleate and Cholesterol pCMVL DNA/TC-Chol complex corresponding to 200 μg of DNA was prepared as described in Example 1 and was mixed with 40 mg of lipids (olive oil: L-α-phosphatidylcholine: L-α-lysophosphatidylcholine: cholesteryl oleate:cholesterol in a 70:22.7:2.3 3.0:2.0 weight ratio) dissolved in chloroform and evaporated under a stream of nitrogen to make a lipid film in a glass tube. Following vacuum desiccation for 1 hour, 1.6 ml of water was added and left at room temperature for 1 hour. The mixture of hydrated lipids and DNA-TC-chol complex was emulsified by vortexing for 2 minutes followed by homogenization for 30 seconds using a Tissue Tearor (Model 985-370, Biospec Product) at 65° C. Finally, the emulsions were extruded 20 times through a polycarbonate membrane with 100 nm pore size (see FIG. 3). The resulting emulsions, designated emulsion formulation #1, were homogeneous particle populations with a mean diameter of 106.9±16.2 nm (average ±s.d., n=3) as measured by light scattering using a submicron particle analyzer (Model N4SD, Coulter Electronics) and are utlized in Example 3–7.

Electrophoresis of emulsion formulation #1 on a 1% agarose gel, followed by staining with ethidium bromide, showed an absence of DNA degradation during incorporation of the hydrophobic DNA/TC-Chol complex into the emulsion.

Figure 4A:
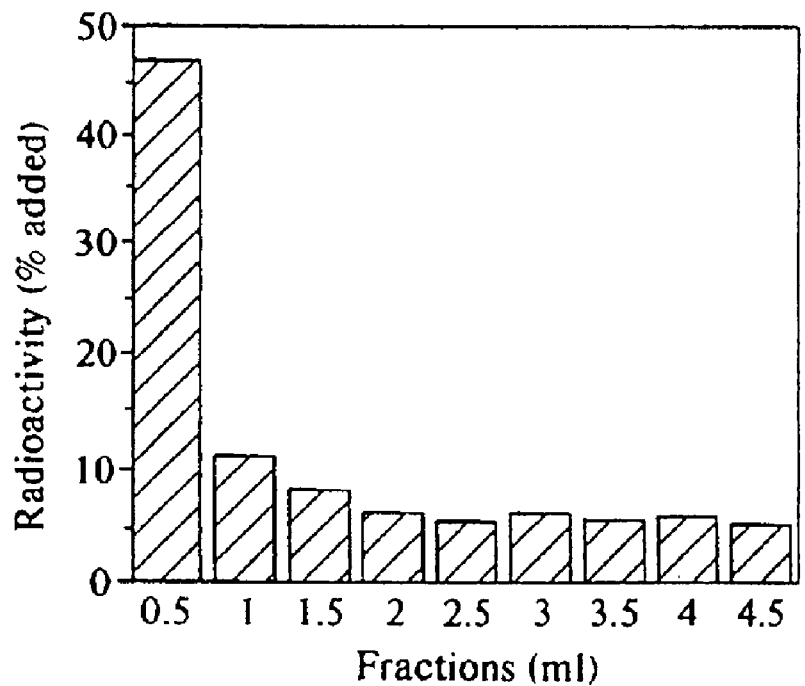
FIGS. 4A and 4B show the distribution of $^{125}$I-labelled DNA incorporated into emulsions as either DNA/TC-chol complex (FIG. 4A) or free DNA (FIG. 4B) following centrifugation. Fractions were collected from the top to the bottom and radioactivity was measured in a gamma counter.
Figure 4B:
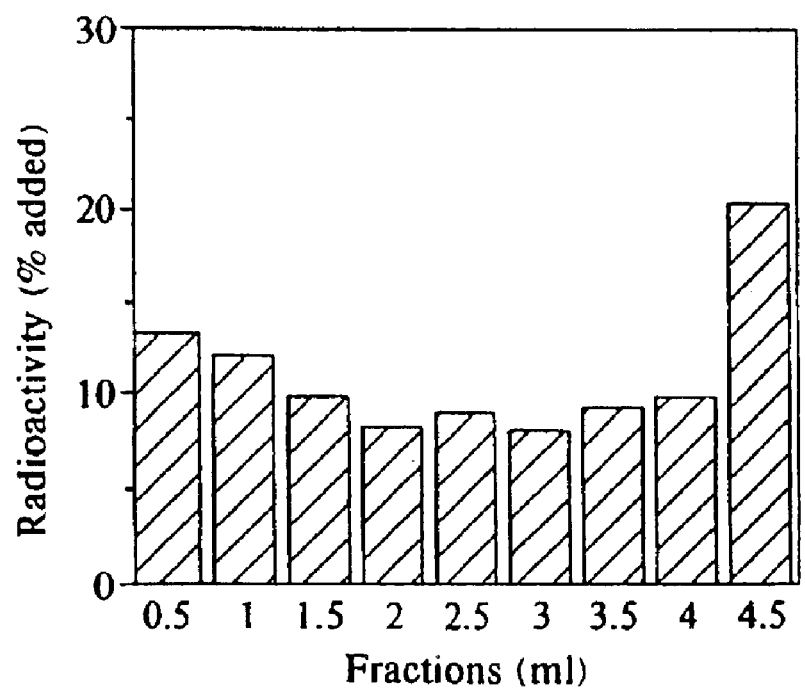

Incorporation of the hydrophobic DNA/TC-Chol complex into emulsion formulation #1 was also confirmed by flotation as follows: the emulsion was diluted with water to a final volume of 4.5 ml and then centrifuged at 16,000×g for 20 minutes at room temperature using an SW 50.1 rotor (Beckman). Half milliliter fractions were then collected from the top to the bottom of the tube and the radioactivity of $^{125}$I-DNA in each fraction was measured. As shown in FIGS. 4A and 4B, more than 80% of DNA added as DNA/TC-Chol complex was floated up with the emulsions into three fractions from the top (FIG. 4A) while when free DNA was used, no flotation of DNA was observed (FIG. 4B). These results indicate that the hydrophobic DNA-TC-chol complex was almost completely incorporated or encapsulated into the emulsions.

Example 2A

Hydrophobic DNA/TC-Chol complexes prepared from 400 μg of DNA and 1.25 mg of TC-Chol by the method described in Example 1A were incorporated into emulsions composed of olive oil: L-α-phosphatidylcholine: L-α-lysophosphatidylcholine: cholesteryl oleate:cholesterol (70:22.7:2.3:3.0:2.0, weight ratio) using the method described in Example 2. Emulsions produced by this method are utilized in Examples 3A, 4A, 5A, 6A, 7A, 7B and 8 and are designated as pCMVL, pLacZ, pRSVHAAT or pAAVC-MVhAAT emulsions depending on the plasmid DNA used to formulate the emulsion.

Figure 12A:
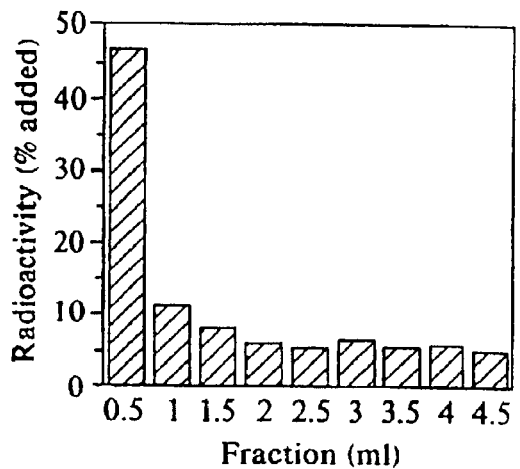
FIGS. 12A–D show the determination of DNA-incorporation into emulsions by centrifugation. DNA/TC-Chol complex (FIGS. 12A and 12C) or free DNA (FIGS. 12B and 12D) supplemented with a trace amount of $^{125}$I-DNA was incorporated into emulsions (FIGS. 12A–C) or mixed with empty emulsions containing TC-Chol (FIG. 12D). The samples (0.5 ml) were centrifuged in 4.5 ml (final) of water (FIGS. 12A and 12B) or NaCl density gradient (FIGS. 12C and 12D). Fractions (0.5 ml) were collected from the top to the bottom of centrifuge tubes and the radioactivities were measured.
Figure 12C:
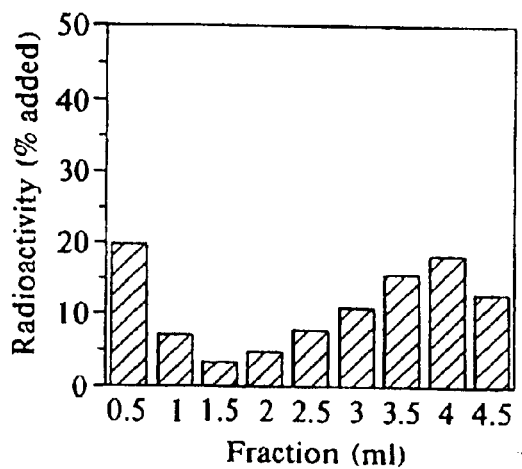
Figure 12B:
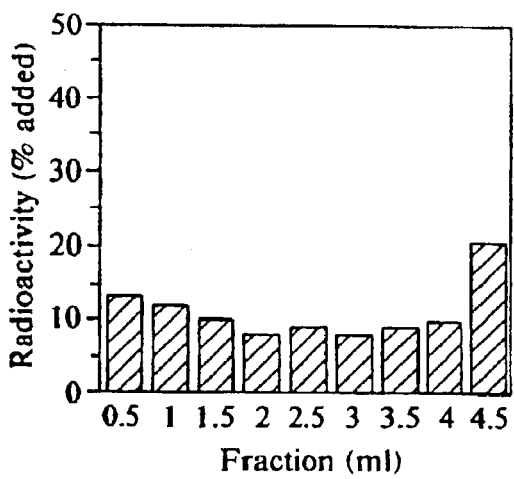

Incorporation of pCMVL DNA (in the form of hydrophobic complexes produced by the method described in Example 1A) into emulsions was determined by its flotation in centrifugation in the absence or presence of a density gradient. After extrusion, 0.5 ml of the emulsion was mixed with 4 ml water and then centrifuged at 16,000×g for 20 min at room temperature using a SW50.1 rotor (Beckman). In the case of the density gradient centrifugation, the emulsion (0.5 ml) was mixed with two-fold volume of NaCl solution with a density of 1.346 and discontinuous gradient was then formed using 1 ml each of NaCl solution with a density of 1.065, 1.020 and 1.006 (Redgrave, T. G. et al. (1985) Biochem. Biophys. Acts 835:104–112). Fractions of a half ml each were collected from the top to the bottom of the centrifuge tube and the radioactivity of $^{125}$I-DNA in each fraction was measured in a gamma counter. More than 65% of DNA added as the complex floated up with the emulsions into the top three fractions (FIG. 12A), whereas no flotation of DNA was observed when free DNA was used (FIG. 12B). This means that more than two thirds of DNA/TC-Chol complexes were incorporated into the emulsions.

Example 3

Characterization of Emulsion Formulations
Emulsion Formulation #1

Since it has been reported that hydrophobic complexes of cationic lipids and DNA are reversibly dissociated in the presence of NaCl at high concentrations [Reimer, D. L., et al. Biochemistry 34, 12877–12883 (1995)], emulsion formulation #1, was mixed with two-fold volume of NaCl solution (d=1.346), and then a discontinuous density gradient was formed using 1 ml each of NaCl solutions (d=1.065, d=1.020 and d=1.006) and centrifuged at 16,000×g for 20 minutes at room temperature using an SW50.1 rotor.

Figure 5A:
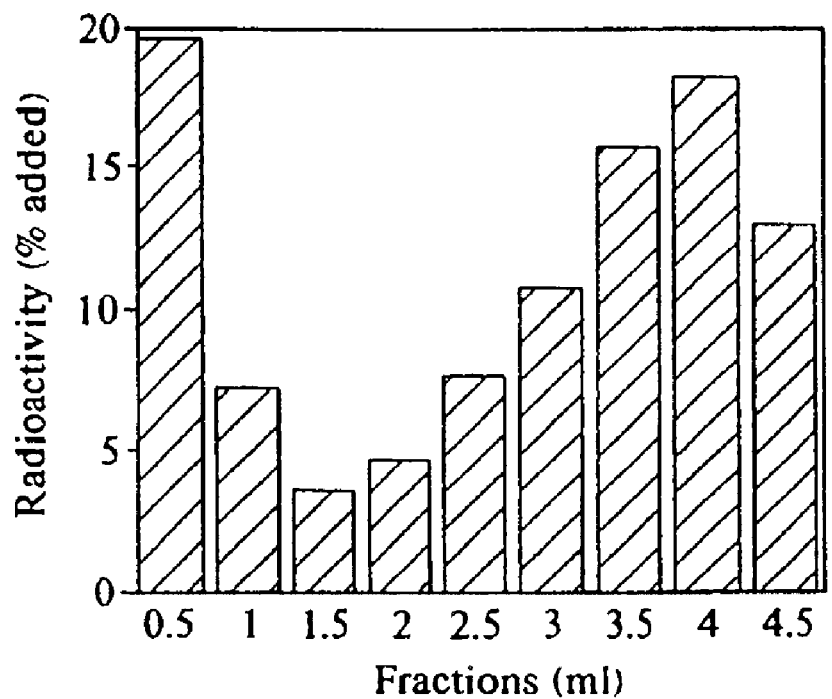
FIGS. 5A and 5B present the distribution in a NaCl density gradient of either $^{25}$I-labelled DNA incorporated into emulsions as $^{125}$I-labelled DNA/TC-chol complex (FIG. 5A) or of free $^{125}$I-labelled DNA mixed with empty emulsions containing the same amount of TC-chol (FIG. 5B). Density gradient fractions were collected from the top to the bottom of the tube and the radioactivity was measured in a gamma-counter.
Figure 5B:
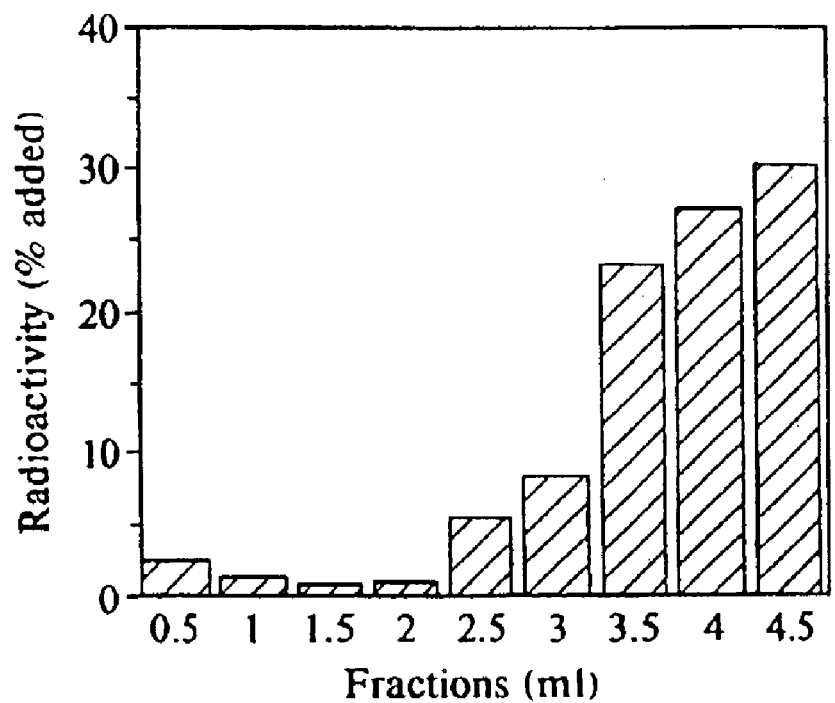

As shown in FIG. 5A, about 32% of $^{125}$I-DNA was recovered in the emulsion fractions at the top of the tube. By comparison, when free DNA was mixed with empty emulsions containing the same amount of TC-chol and treated by density gradient centrifugation, no DNA was found in the emulsion fractions (FIG. 5B).

Figure 12D:
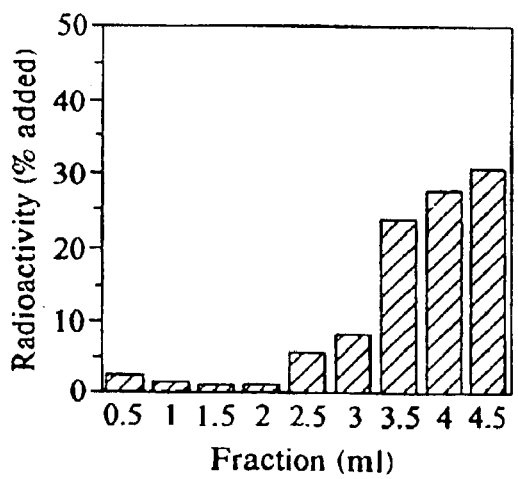

Example 3A pCMVL Emulsions pCMVL emulsions were also mixed with NaCl solution and then density gradient centrifugation was carried out. About 32% of DNA was recovered from the upper emulsion fractions (FIG. 12C). When free DNA was mixed with empty emulsions containing TC-Chol in its lipid composition, the majority of DNA associated with the emulsion, resulting in flotation after the centrifugation in the water (data not shown). However, no flotation of DNA was observed after the NaCl density gradient centrifugation (FIG. 12D). Thus, at least 50% of DNA incorporated into emulsion is likely to be localized in the internal space of the emulsion. Resulting DNA/TC-Chol-emulsions had a homogeneous particle distribution with a mean diameter of 107±16 nm (average ±s.d., n=3) measured by light scattering using a submicron particle analyzer (N4 Plus, Coulter Electronics).

Example 4

Animal Studies With Emulsion Formulations

Emulsion Formulation #1

In order to evaluate whether the emulsion formulation #1 could act as an effective gene delivery system in vivo, mice were injected intraportally with either emulsion formulation (corresponding to 100 µg pCMVL DNA) dissolved in 1 ml of isotonic mannitol solution, 100 µg naked DNA dissolved in isotonic mannitol solution or 100 µg naked DNA dissolved in hypertonic solution (15% mannitol, 0.9% NaCl).

Two days after injection, the mice were sacrificed and the liver, spleen, lung, kidney and heart were collected. Luciferase activity in Examples 4, 5, 6 and 7 was determined as follows: Organs were homogenized with lysis buffer (0.05% Triton X-100, 2 mM EDTA, 0.1 M Tris, pH 7.8). After two cycles of freeze (liquid nitrogen)-thaw (at 30C), the homogenates were centrifuged at 14,000 rpm for 10 minutes at 4° C. Twenty microliter of the supernatant was mixed with 100 µl of Luciferase Assay System (Promega) and relative light unit (RLU) was measured with a Luminometer (AutoLumat LB953, EG&G, Berthold). Conversion from RLU to luciferase protein mass was calculated from a standard curve (0.01 to 1.0 ng; ng luciferase=(RLU+1975.4)/3.5553×10$^4$) ) based on purified luciferase protein standards (Sigma). Protein concentration was also determined by a Coomassie Plus Protein Assay Reagent (Pierce), using BSA as a standard.

Figure 6:
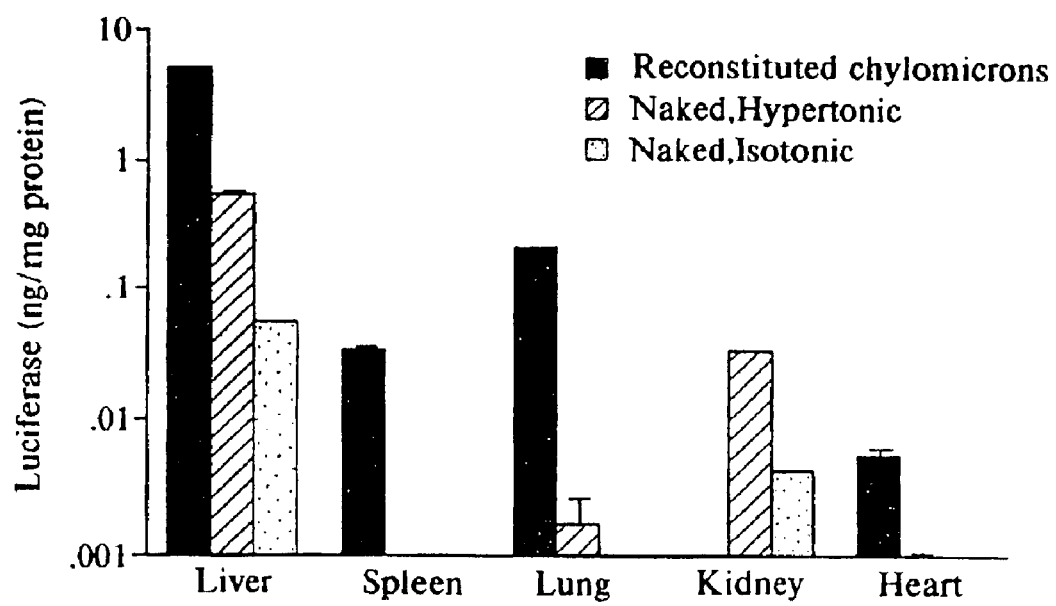
FIG. 6 illustrates the production of luciferase proteins in the indicated organs of mice following portal vein injection of either 100 μg of naked DNA dissolved in hypertonic solution, 100 μg of naked DNA dissolved in isotonic solution, or 100 μg of DNA in the form of emulsions produced by mixing plasmid pCMVL DNA/TC-Chol complex with olive oil, phosphatidylcholine, lysophosphatidylcholine, cholesteryl oleate and cholesterol as described in FIG. 3. The number of mice used in each experiment described in FIGS. 6–10 are indicated in parentheses in FIGS. 6–10 as n=_____.

As shown in FIG. 6, high amounts of luciferase protein were produced in the livers of mice injected intraportally with the emulsions while the production of luciferase protein was almost 100-fold lower for injection of naked DNA in isotonic solution and 10-fold lower for infection of naked DNA-hypertonic injection solution (15% mannitol, 0.9% NaCl).

In addition, while luciferase protein was also produced in the spleen, lung and heart of mice injected with emulsion formulation #1, the level of expression was 25- to 800-fold less than the liver. In the case of naked DNA, substantial luciferase production was also found in the kidney. Finally, since total liver extract contained about 170 mg of protein, it appeared that more than 800 ng of luciferase protein was produced in the entire liver of the emulsion-injected mice.

Figure 7:
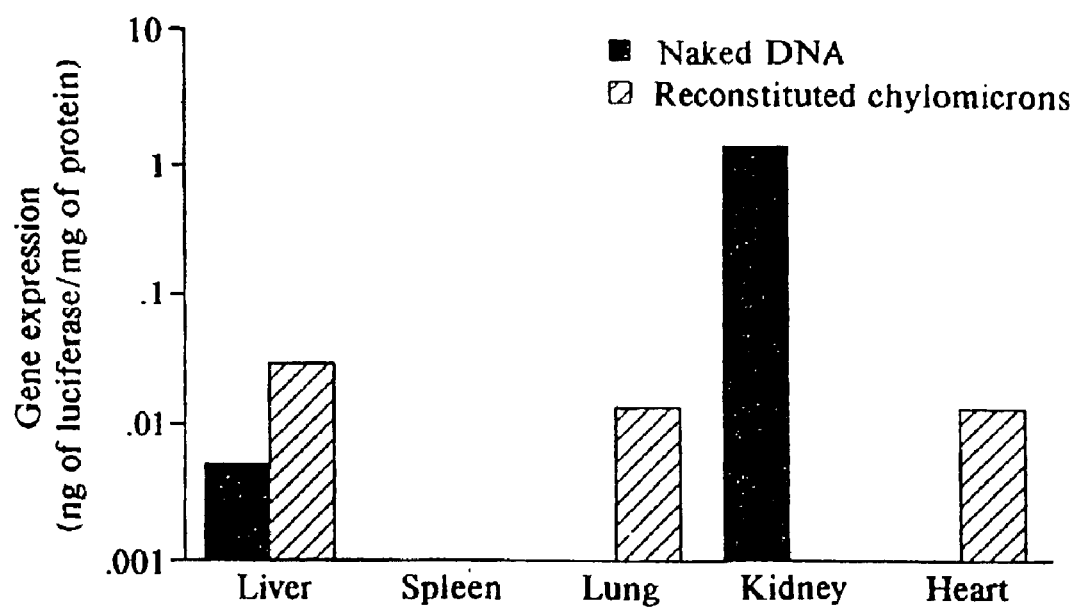
FIG. 7 shows the production of luciferase proteins in the indicated organs of mice following tail vein injection of 100 μg DNA in the form of either naked DNA or emulsions produced by mixing plasmid pCMVL DNA/TC-Chol complex with olive oil, phosphatidylcholine, lysophosphatidylcholine, cholesteryl oleate and cholesterol as described in FIG. 3.

By comparison, as shown in FIG. 7, the level of luciferase protein produced in the liver of the mouse injected in the tail vein with emulsion formation #1 (corresponding to 100 µg PCMVL DNA) was much lower than that observed in the livers of mice injected intraportally with emulsion formulation #1 (compare FIG. 7 with FIG. 6). However, as for the intraportally injected mice, the tail vein-injected mouse also showed greater luciferase production (about 6-fold) in the liver when injected with emulsions as compared to naked DNA (FIG. 7). In addition, much higher production of luciferase protein was found in the kidney than in the liver in the case of injection of naked DNA (FIG. 7).

In sum, higher gene expression was obtained when the emulsions were injected into the portal vein rather in the tail vein.

Example 4A pCMVL Emulsions

Mice were injected intraportally with 100 µg DNA of pCMVL emulsions produced as described in Example 2A and 2 days after injection, the mice were sacrificed and liver, spleen, lung, kidney and heart were collected. Luciferase activity for Examples 4A, 5A, 6A and 7A was determined as follows: Organs were homogenized with lysis buffer (0.05% Triton X-100, 2 mM EDTA, 0.1 M Tris, pH 7.8) using a Tissue Tearor for 1 min. After 2 cycles of freeze in liquid nitrogen and thaw at 37° C., the homogenates were centrifuged at 14,000×g for 10 min at 4° C. Twenty µl of the supernatant were mixed with 100 µl of Luciferase Assay System and relative light unit (RLU) was measured with a luminometer (AutoLumant LB 953, EG&G) for 20 seconds Conversion from RLU to luciferase protein mass was calculated from a standard curve (1 to 10,000 pg; pg luciferase=−5.0+8.3×10$^{-3}$×RLU, r$^2$=0.99) based on purified luciferase protein as a standard. Protein concentration of the supernatant was also determined by a Coomassie Protein Assay Reagent, using bovine serum albumin as a standard.

Figure 13:
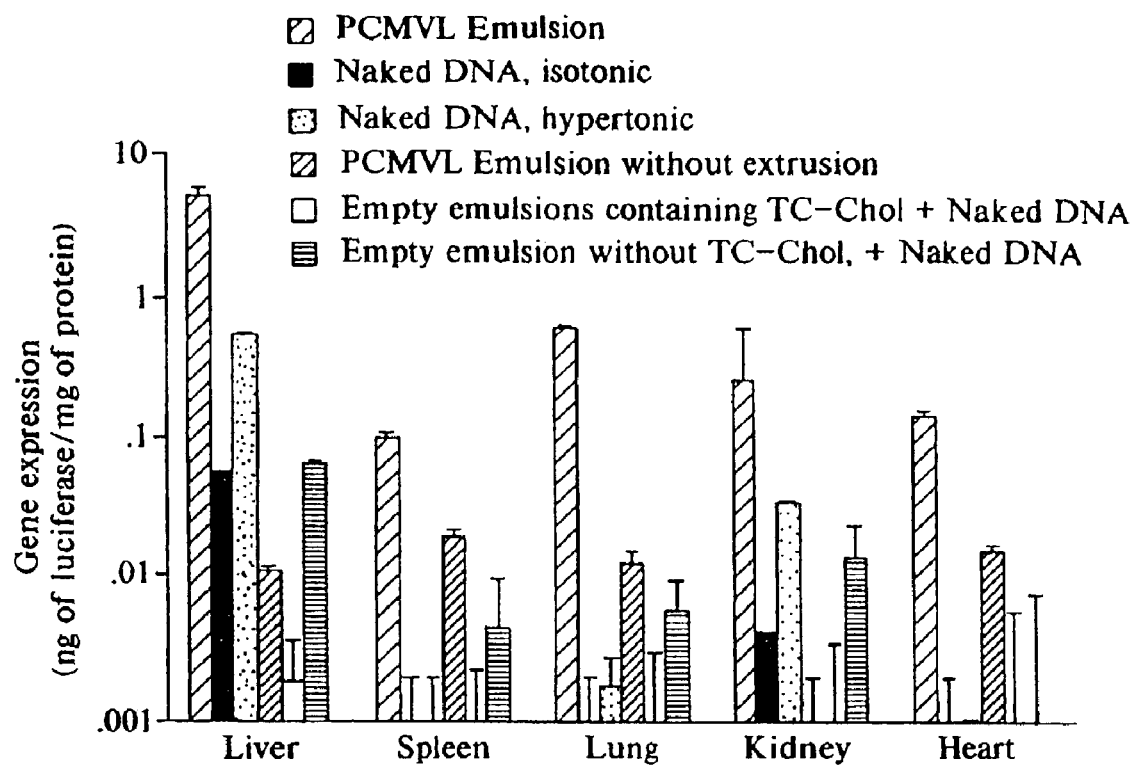
FIG. 13 shows gene expression in organs of mice following intraportal injection. CD1 mice were intraportally injected with 100 µg of plasmid pCMVL DNA in the various formulations. Two days after injection, mice were sacrificed and luciferase activity and protein concentration of tissue extracts were analyzed. Each column presents the mean from three animals ±s.d.

As shown in FIG. 13, a high amount of luciferase protein was produced in the liver. The level was almost 100-fold higher than that of naked DNA-injected mice (Naked DNA, isotonic). Although the level of gene expression in the liver by naked DNA was significantly increased when a hypertonic solution (15% mannitol, 0.9% NaCl) was used for injection (Naked DNA, hypertonic) the level was still 10-fold lower than that of the pCMVL emulsions. Luciferase protein was also produced in the spleen, lung and heart by intraportal injection of PCMVL emulsions, but the levels were 25- to 800-fold less than that in the liver. The particle size of the pCMVL emulsions was important for an efficient gene delivery into hepatocytes. Injection of pCMVL emulsions without extrusion (pCMVL emulsion without extrusion) which had a mean diameter of 352±135 nm, resulted in a low level of the luciferase protein production in the liver, spleen, lung and heart. The necessity of DNA incorporation into the interior of the emulsion was also examined by preparing empty emulsions with or without TC-Chol, and then mixed with 100 µg of pCMVL DNA and injected. The emulsions containing TC-Chol formed aggregations immediately after the addition of DNA (TC-Chol-emulsion, DNA), and showed no gene expression in any organs. In the case of the mixture of DNA and empty emulsion without TC-Chol (emulsion, DNA), gene expression in each organ was almost the same as that of the mice injected with only naked DNA (Naked DNA, isotonic). These results indicate that high level of gene expression requires the location of DNA in the interior of the emulsion.

Example 5

In Vivo Gene Expression Following Portal Vein Injection Into Mice Of Naked pCMVL DNA or of Various Formulations Containing pCMVL DNA One hundred micrograms of DNA in the form of naked DNA, emulsion formulation #1, emulsion formulation #1 without extrusion, empty emulsions containing TC-Chol and naked DNA, or empty emulsions without TC-Chol and naked DNA, were injected intraportally into mice and two days after injection, the mice were sacrificed and luciferase activity in various organs was assayed.

Figure 8:
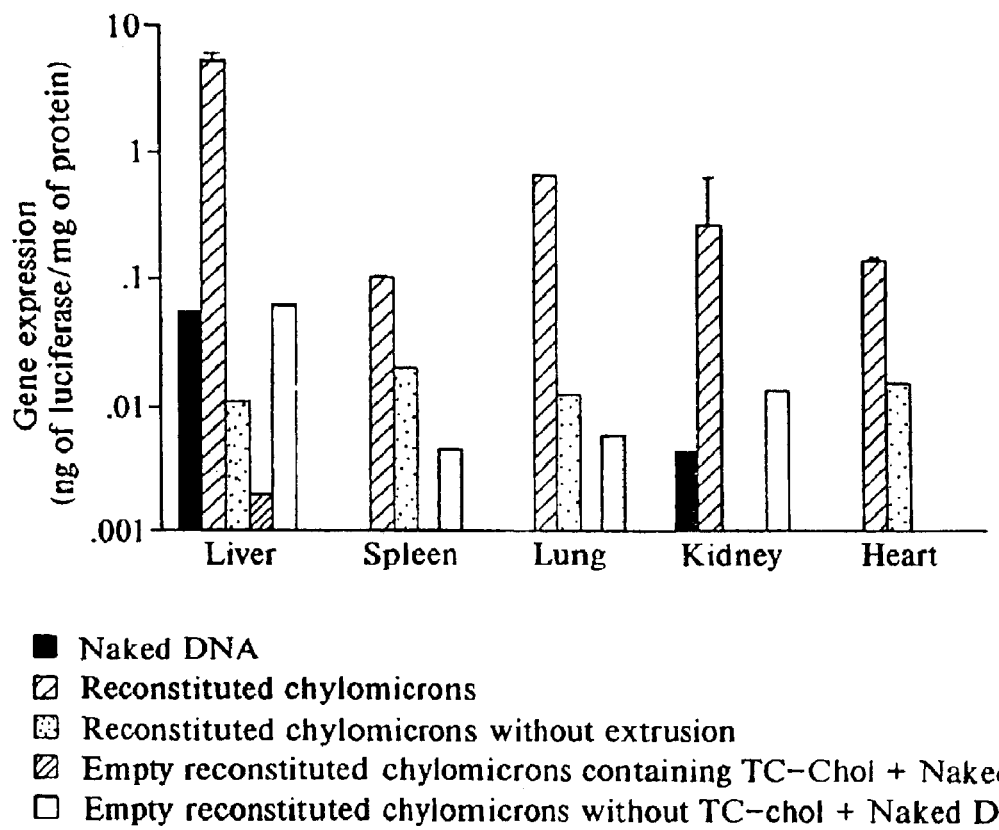
FIG. 8 shows production of luciferase proteins in the indicated organs of mice following portal vein injection of 100 μg of plasmid pCMVL DNA as the various formulations indicated in the Figure.

The results presented in FIG. 8 show that as in Example 4 (see FIG. 6), a high amount of luciferase protein was produced in the liver following injection of emulsion formulation #1 and the level was almost 100-fold higher than that observed for naked DNA.

Of interest, when emulsion formulation #1 without extrusion was injected, production of luciferase protein in the liver was low (FIG. 8) (almost same as that in the spleen, lung and heart), suggesting that extrusion through a polycarbonate membrane with 100 nm pore size is necessary to prepare active reconstituted chylomicrons which are able to pass through fenestration of sinusoidal wall of liver and gain access to the hepatocytes. Moreover, TC-Chol-containing emulsions formed aggregations immediately after the addition of DNA, and did not show production of luciferase protein in any organs (FIG. 8) while in the case of the mouse injected with naked DNA mixed with emulsions not containing TC-Chol, the production of luciferase protein in each organ was almost the same level as that of the mouse injected with only naked DNA (FIG. 8).

Example 5A pCMVL Emulsions

Figure 14:
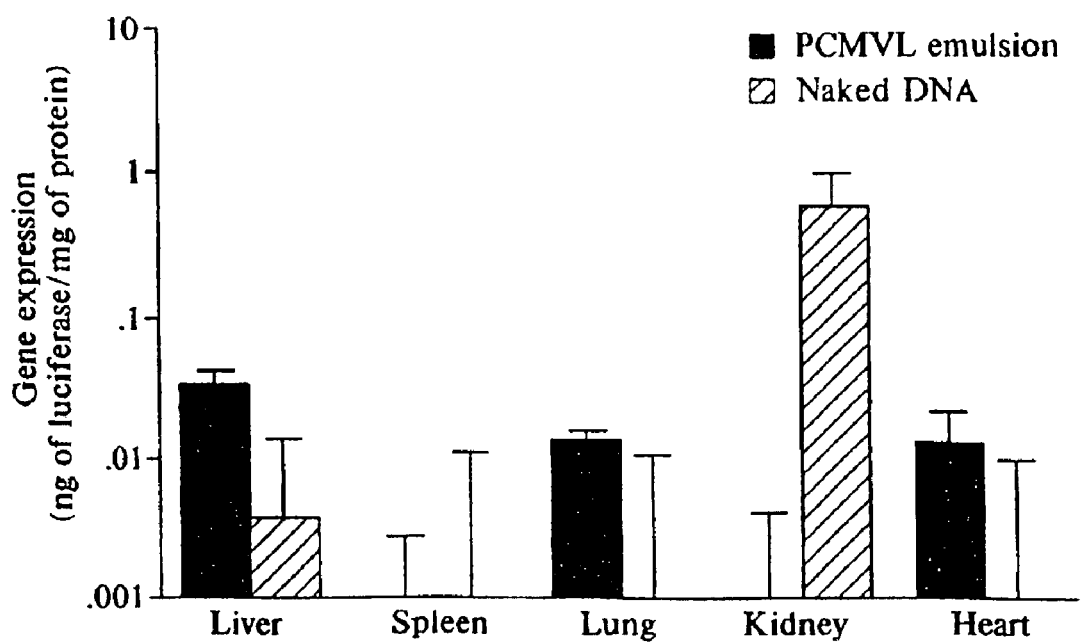
FIG. 14 shows gene expression in organs of mice following intravenous injection. Mice were injected from the tail vein with naked pCMVL DNA or with pCMVL emulsions at the dose of 100 µg of DNA. Two days after injection, mice were sacrificed and luciferase activity in the various organ extracts was measured. Each column presents the mean from three animals ±s.d.

Distribution and strength of gene expression after tail vein injection was also examined in mice (FIG. 14) two days after injection of 100 μg DNA of pCMVL emulsion. Gene expression is the highest in the liver and also in the lung and heart. The level of gene expression in the liver was significantly higher as compared with naked DNA, but was almost 100-fold lower than that of the mice injected intraportally (FIG. 14).

Example 6

Gene Expression in the Organs of Mice Following Portal Vein Injection with Various Amounts of Emulsion Formulations

Emulsion Formulation #1

Mice injected intraportally with 0, 10, 25, 50, 75 or 100 μg of DNA in the form of emulsion formulation #1 were sacrificed two days post-injection and luciferase activity in was assayed liver, spleen, lung, kidney, and heart.

Figure 9:
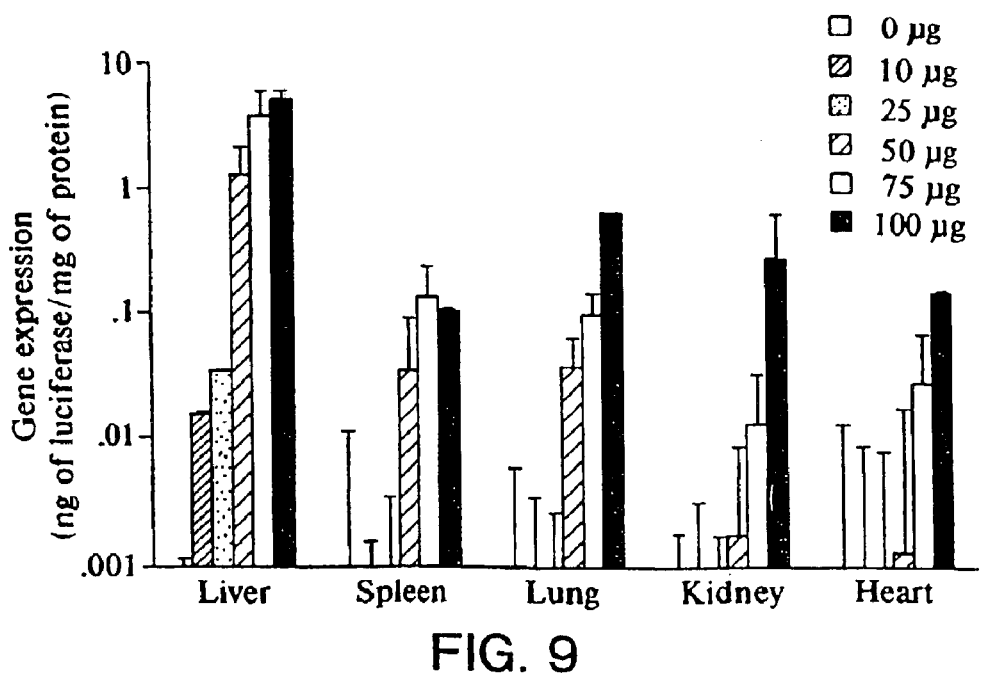
FIG. 9 shows the production of luciferase proteins in the indicated organs of mice following portal vein injection of the indicated amounts of pCMVL DNA in the form of emulsions produced by mixing plasmid pCMVL DNA/TC- Chol complex with olive oil, phosphatidylcholine, lysophosphatidylcholine, cholesteryl oleate and cholesterol as described in FIG. 3.

As shown in FIG. 9, production of luciferase protein in each organ increased with each increase in the injected dose and gene expression in the liver was almost saturated with injection of 50 μg of DNA in the form of emulsion formulation #1.

Example 6A pCMVL Emulsions

Figure 15:
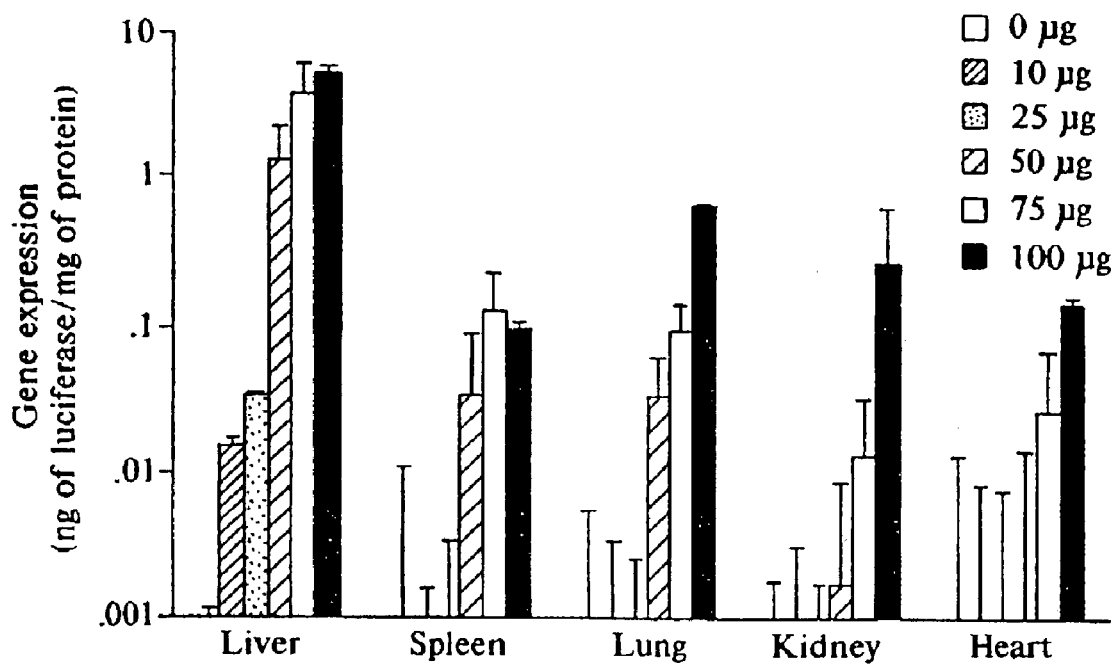
FIG. 15 shows the dose dependence of gene expression by intraportal injection of various amounts of pCMVL emulsions into mice. Luciferase activity in the extracts from various organs was measured on day 2. Each column presents the mean from three animals ±s.d.

The effect of injected dose on the gene expression in mice following intraportal injection by pCMVL emulsion was also examined (FIG. 15). Even by injection of 10 μg of DNA, pCMVL emulsion induced a measurable level of gene expression in the liver. The level of gene expression in each organ increased with increasing injected dose. In the liver, the gene expression jumped up between 25 and 50 μg of DNA and was almost saturated with 100 μg of DNA.

Figure 16:
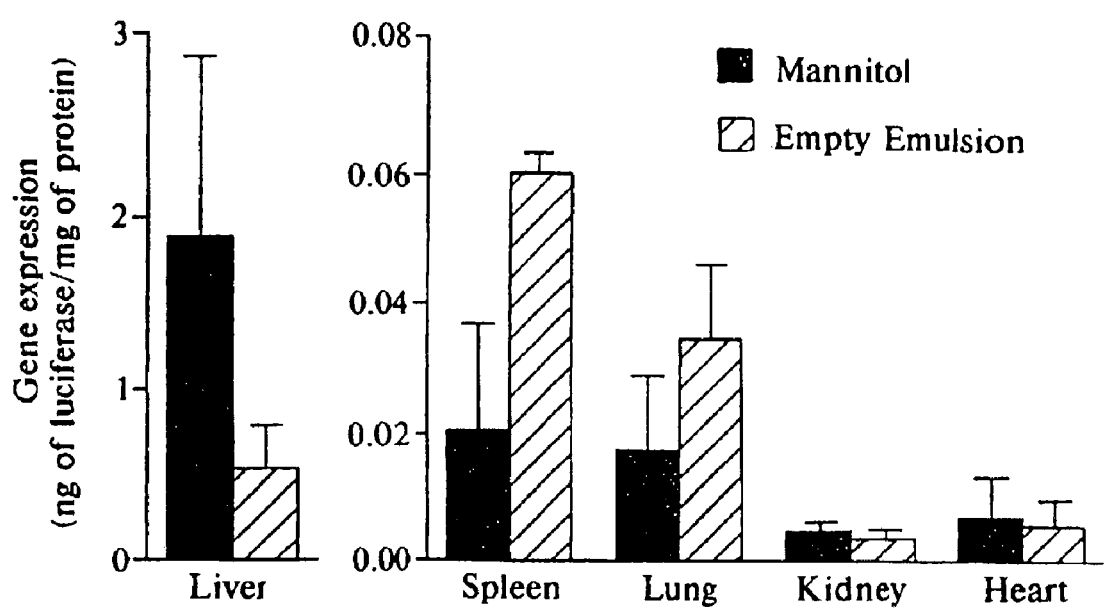
FIG. 16 shows the effect of pre-injection of empty emulsions on gene delivery by pCMVL emulsions. Fifteen minutes after intraportal injection of 0.6 ml of isotonic mannitol with or without empty emulsions (5.0 mg of total lipids), mice were intraportally injected with 50 µg DNA of pCMVL emulsion dispersed in 0.6 ml of isotonic mannitol. Two days after injection, mice were sacrificed and luciferase activity in the various organ extracts was measured. Each column presents the mean from three animals ±s.d.

To reveal whether the gene expression in the liver results from uptake of emulsion particles themselves or not, the effect of empty emulsion pre-injection on the gene expression was investigated (FIG. 16). Gene expression in the liver by injection of 50 μg DNA of PCMVL emulsions was reduced to about one-third by pre-injection of empty emulsion at the dose corresponding to 100 μg DNA in pCMVL emulsions. However, the effect in the spleen and lung was opposite, i.e. three fold increase in the spleen and two fold increase in the lung. No effect was observed in the kidney and heart.

Example 7

Time Course of Gene Expression in Mice Injected Intraportally with Various Emulsion Formulations

Emulsion Formulation #1

Fifty μg of DNA was intraportally injected as emulsion formulation #1 and the mice were sacrificed 1, 2, 3, 4, 5, 6 or 7 days after injection and luciferase activity in liver, spleen, lung, kidney, and heart was assayed.

Figure 10:
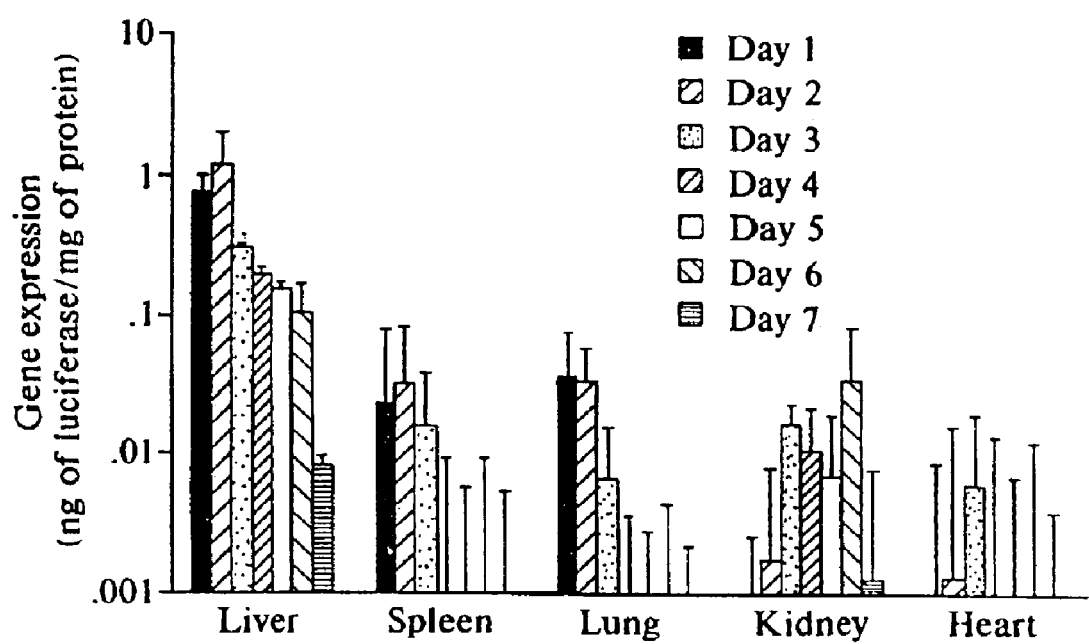
FIG. 10 presents the results of a time course of luciferase protein expression in the indicated organs of mice following portal vein injection of 50 µg of plasmid pCMVL DNA in the form of emulsions produced by mixing DNA/TC-Chol complex with olive oil, phosphatidylcholine, lysophophatidylcholine, cholesteryl oleate and cholesterol as described in FIG. 3.

As shown in FIG. 10, gene expression reached maximum level on day 2 except for the kidney and after day 2, the expression was gradually reduced and almost disappeared on day 7 in the liver and kidney, and on day 4 in the spleen, lung and heart.

Example 7A pCMVL Emulsions

Figure 17:
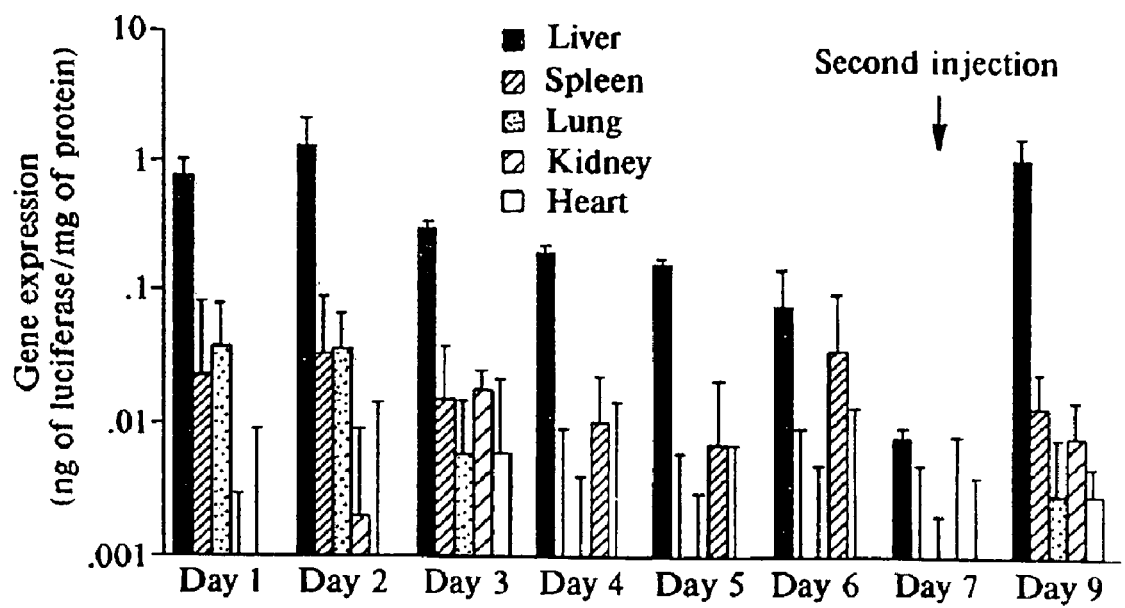
FIG. 17 shows the time course of gene expression after first and second injections. Mice were intraportally injected with 50 µg DNA of pCMVL emulsions and sacrificed on the indicated day after injection. Some of them were injected again at day 7 by the same method as the first injection and were sacrificed 2 days after the second injection. Luciferase activity in the various organ extracts was measured. Each column presents the mean from three animals ±s.d.

FIG. 17 shows the time course of gene expression at the dose of 50 μg of pCMVL-DNA injected intraportally. High level of gene expression was observed at day 1 and day 2 in the liver, but there was a significant reduction at day 3 (FIG. 17). After that, gene expression in the liver gradually decreased and almost disappeared by day 7. Other organs except the kidney showed similar time course of change in gene expression. The kidney retained a constant level of gene expression from day 2 to day 6. FIG. 17 also shows the possibility of repetitive injection of pCMVL emulsion since two days after the second injection at day 7, comparable gene expression to that obtained after the first injection was observed in the liver.

Example 7B pRSVhAAT and pAAVCMVhAAT Emulsions

Figure 18:
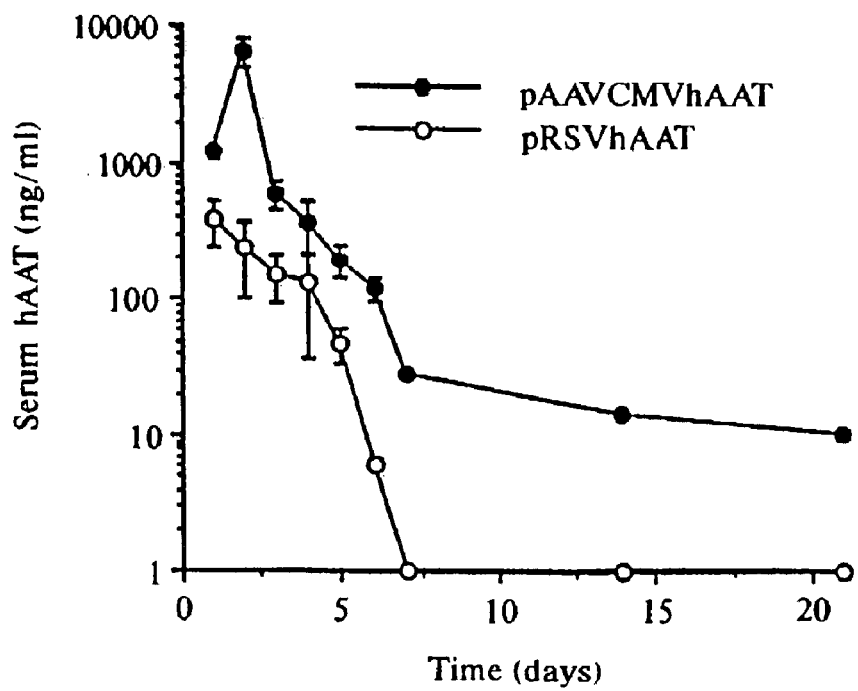
FIG. 18 shows the delivery and expression of hATT gene by emulsions. Mice were intraportally injected with 50 µg DNA of pRSVhAAT emulsions or pAAVCMVhAAT emulsions. At the indicated days after injection, blood was collected from the tail vein of mice and serum concentration of hAAT was determined by ELISA. Each point presents the mean from three animals ±s.d.

Another time course experiment was carried out using two different plasmids containing HAAT gene driven by a different promoter (FIG. 18). In both cases, significant amount of hAAT was produced and secreted into the blood circulation. pAAVCMVhAAT, however, produced the highest serum level (6 μg/ml) of hAAT at day 2, which was 17 fold higher than the highest serum HAAT level achieved at day 1 after injection of the same dose of pRSVhAAT. Moreover, although the serum level of hAAT rapidly decreased by 7 days after injection of both DNA, detectable concentration of hAAT was constantly observed until 60 days after injection of pAAVCMVhAAT (data not shown).

Example 8

Histochemical Analysis of Gene Expression in the Liver

Figure 19:
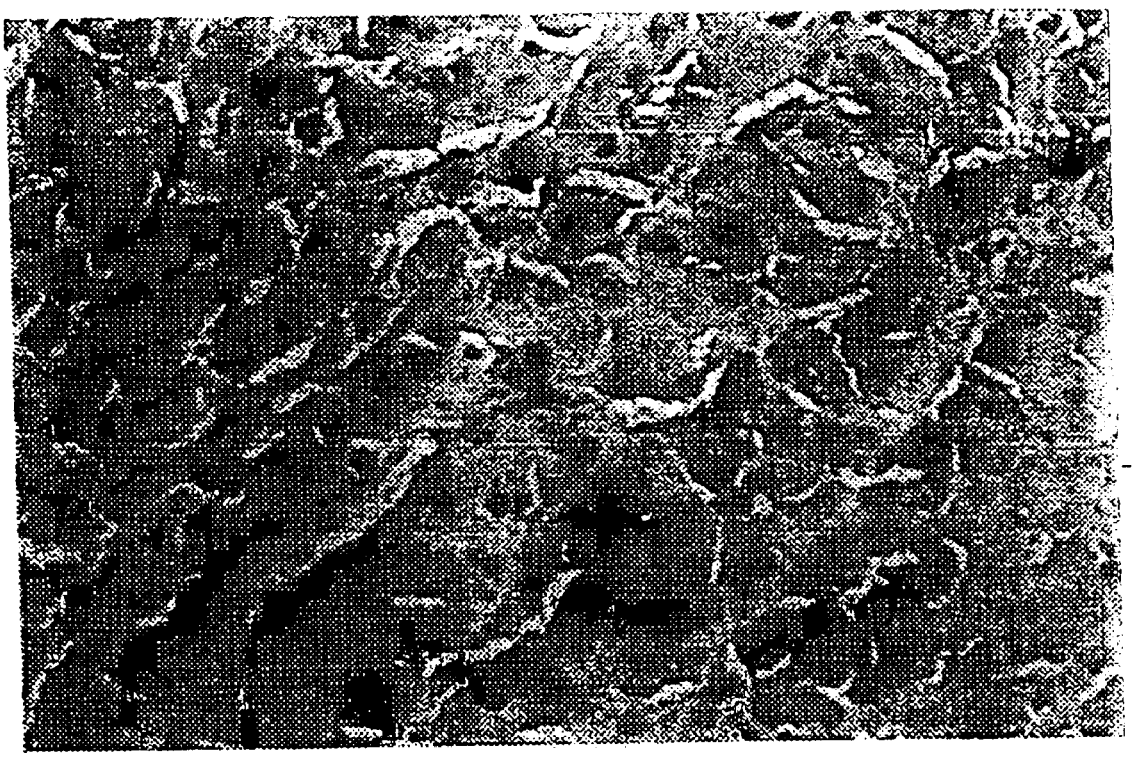
FIG. 19 shows X-Gal staining of liver section from a mouse injected with pCMVLacZ emulsion. A mouse was intraportally injected with 100 µg DNA of pCMVLacZ emulsion. Two days after injection, liver cryosections of 10 µm in thickness were stained with X-Gal for 24 h. After counter sections were examined under a light microscope (Diaphot, Nikon) at an original magnification of ×400.

To elucidate the population and localization of cells in the liver which are transfected by intraportal injection of pCMVLacZ emulsions, pCMVLacZ DNA was complexed with TC-ChoL and incorporated into emulsions (pCMVLacZ emulsion) as described in Example 2A and injected into a mouse. Liver cells expressing β-Gal activity were visualized by X-Gal staining (FIG. 19). Liver sections from a control (isotonic mannitol-injected) mouse or mouse injected with naked DNA did not show any change in color, while the color of liver sections from a mouse injected with pCMV-LacZ emulsions turned to blue. By microscope examination of the liver cryosections from a control mouse, no β-Gal positive cell was observed (photo not shown). However, approximately 10% of the cell population was stained by X-Gal and these blue cells were found all over the section. It appeared at higher magnification that these cells were not only hepatocytes, which have a polygonal shape and round nuclei, but also nonparenchymal cells (FIG. 19).

What is claimed is:

1. An emulsion formulation comprising triglycerides, cholesterol, phospholipids, at least one cationic lipid, at least one hydrophilic biologically active molecule and an aqueous carrier, wherein the hydrophilic biologically active molecule is a nucleic acid molecule, wherein the cationic lipid forms a hydrophobic complex with the nucleic acid that is encapsulated within an apolar core comprising said triglycerides, and wherein the phospholipids form an outer layer surrounding the apolar core.

2. A method for delivering a nucleic acid to cells, said method comprising exposing the cells to the emulsion formulation of claim 1, thereby facilitating the delivery of the nucleic acid to the cells, wherein the cells are exposed to the emulsion formulation in vivo by administering the emulsion formulation to an animal in an amount effective to facilitate the delivery of the nucleic acid to the cells of the animal.

3. A method for delivering a nucleic acid to cells, said method comprising exposing the cells to the emulsion formulation of claim 1, thereby facilitating the delivery of the nucleic acid to the cells, wherein the cells are exposed to the emulsion formulation in vitro.

* * * * *